United States Patent
Freeman et al.

(10) Patent No.: US 11,031,120 B1
(45) Date of Patent: Jun. 8, 2021

(54) SYSTEM, METHOD, AND NON-TRANSITORY COMPUTER-READABLE STORAGE MEDIA RELATED TO CORRECTION OF VISION DEFECTS USING A VISUAL DISPLAY

(71) Applicant: Raytrx, LLC, Tulsa, OK (US)

(72) Inventors: Richard C. Freeman, Tulsa, OK (US); Michael H. Freeman, Tulsa, OK (US); Mitchael C. Freeman, Sapulpa, OK (US); Chad Boss, Tulsa, OK (US); Jordan Boss, Tulsa, OK (US)

(73) Assignee: RAYTRX, LLC, Tulsa, OK (US)

( * ) Notice: Subject to any disclaimer, the term of this patent is extended or adjusted under 35 U.S.C. 154(b) by 0 days.

(21) Appl. No.: 17/151,174

(22) Filed: Jan. 17, 2021

Related U.S. Application Data

(63) Continuation of application No. 17/137,093, filed on Dec. 29, 2020, which is a continuation-in-part of
(Continued)

(51) Int. Cl.
| | |
|---|---|
| *G06K 9/00* | (2006.01) |
| *A61B 3/14* | (2006.01) |
| *G16H 30/40* | (2018.01) |
| *G16H 10/60* | (2018.01) |
| *A61B 3/032* | (2006.01) |

(Continued)

(52) U.S. Cl.
CPC ........... *G16H 30/40* (2018.01); *A61B 3/0025* (2013.01); *A61B 3/024* (2013.01); *A61B 3/032* (2013.01); *A61B 3/12* (2013.01); *G16H 10/60* (2018.01); *G16H 30/20* (2018.01); *G16H 50/20* (2018.01); *A61F 9/08* (2013.01)

(58) Field of Classification Search
USPC ........ 382/100, 103, 106–107, 114, 117, 123, 382/128, 155, 162, 172–173, 181, 199, 382/219, 224, 232, 254, 274, 276, 382/287–291, 305, 321; 345/8; 351/210, 351/224, 209, 159.52
See application file for complete search history.

(56) References Cited

U.S. PATENT DOCUMENTS

| | | | | |
|---|---|---|---|---|
| 7,600,873 | B2 * | 10/2009 | Grundig | A61B 3/0025 351/210 |
| 9,072,888 | B2 * | 7/2015 | Greenberg | A61N 1/0543 |

(Continued)

OTHER PUBLICATIONS

Computer vision detection of defective apples using automatic lightness correction and weighted RVM classifier (2015) (Year: 2015).*

*Primary Examiner* — Seyed H Azarian
(74) *Attorney, Agent, or Firm* — Head, Johnson, Kachigian & Wilkinson, PC

(57) ABSTRACT

A method of at-home monitoring of eye conditions using a head mounted display that is capable of establishing a visual model associated with a patient. The visual model may include data related to a quality of the patient's vision. The patient may use the system to establish a visual model periodically, such as daily, and the system may compare the visual model to previous visual models and send an alert to the patient's physician if changes meeting a given criteria are detected. This may allow the physician to immediately take steps to save the patient's eyesight where a delay in treatment may result in vision loss.

9 Claims, 16 Drawing Sheets

Related U.S. Application Data application No. 16/173,719, filed on Oct. 29, 2018, now Pat. No. 10,874,297, which is a continuation of application No. 15/940,561, filed on Mar. 29, 2018, now Pat. No. 10,111,583, which is a continuation of application No. 15/073,144, filed on Mar. 17, 2016, now Pat. No. 9,955,862.

(60) Provisional application No. 62/134,422, filed on Mar. 17, 2015.

(51) Int. Cl.
*A61B 3/024* (2006.01)
*A61B 3/00* (2006.01)
*A61B 3/12* (2006.01)
*G16H 50/20* (2018.01)
*G16H 30/20* (2018.01)
*A61F 9/08* (2006.01)

(56) References Cited

U.S. PATENT DOCUMENTS

| 2007/0121070 A1* | 5/2007 | Alster | A61B 3/024 351/224 |
| 2014/0184475 A1* | 7/2014 | Tantos | H03M 13/356 345/8 |
| 2017/0135577 A1* | 5/2017 | Komogortsev | A61B 3/14 |
| 2019/0201693 A1* | 7/2019 | Nirenberg | A61N 1/36046 |

* cited by examiner

SYSTEM, METHOD, AND NON-TRANSITORY COMPUTER-READABLE STORAGE MEDIA RELATED TO CORRECTION OF VISION DEFECTS USING A VISUAL DISPLAY

CROSS-REFERENCE TO RELATED APPLICATIONS

This application is a continuation of U.S. patent application Ser. No. 17/137,093 filed Dec. 29, 2020, which is a continuation-in-part of U.S. patent application Ser. No. 16/173,719 filed Oct. 29, 2018, which claims priority to and the benefit of U.S. Patent Application Ser. No. 62/134,422, filed on Mar. 17, 2015, U.S. patent application Ser. No. 15/073,144 filed Mar. 17, 2016, and U.S. patent application Ser. No. 15/940,561 filed Mar. 29, 2018, the disclosures of which are hereby incorporated by reference.

FIELD OF THE DISCLOSURE

The present invention relates generally to the correction of vision defects, and more specifically, to a system, and methods for compensating for visual defects for detecting the vision defects, capturing an image, correcting the image and displaying a corrected image.

BACKGROUND

Macular degeneration and other FOV (Field of Vision) related blindness or vision defect conditions, such as end-stage glaucoma, Stargardt's disease, central serous retinopathy, myopic macular degeneration, diabetic macular edema, cystoid macular edema, macular holes, macular atrophy, anterior ischemic optic neuropathy and retinitas pigmentosa are often irreversible. The impact to a patient's life due to the loss of a portion of their vision is enormous, including degraded and loss of the ability to read, watch TV and see computer screens. Some of the conditions can be halted, and fortunately leaves some of the vision intact, and in the case of Macular Degeneration, the peripheral vision remains intact.

There have been previous attempts to augment the sight of a patient whose other sight is defective or otherwise impaired, or otherwise compensate for the patient's damaged or impaired sight. For instance, previous efforts have focused on the devices that increase the intensity or contrast of the patient's sight and/or increase the magnification of the image seen by the patient. These attempts have not been very effective and are bulky and expensive.

The present invention is aimed at one or more of the problems identified above.

SUMMARY OF THE INVENTION

In one embodiment, a system having a database, a model controller, a display controller and a display unit is provided. The model controller is coupled to the database and is configured to establish a visual model associated with a patient and to store the visual model in the database. The visual model includes data related to a quality of the patient's vision. The model controller is further configured to establish a boundary as a function of data associated with the visual model. The boundary is indicative of an area to be corrected within the patient's vision. The model controller is further configured to establish a retinal map as a function of the boundary and to store the retinal map in the database. The display controller is configured to receive and to store the retinal map. The display controller is further configured to receive an image from a camera or cameras from associated with the patient and to apply corrections to the image based on the retinal map and responsively generate a corrected image. The display unit is coupled to the display controller and is configured to receive the corrected image to present the corrected image to the eye of the patient.

In other embodiments, a method is provided. The method includes the steps of establishing, by a model controller, a visual model associated with a patient and storing the visual model in the database. The visual model includes data related to a quality of the patient's vision. The method further includes the step of establishing, by the model controller, a boundary as a function of data associated with the visual model, the boundary being indicative of an area to be corrected within the patient's vision. The method also includes the steps of establishing, by the model controller, a retinal map as a function of the boundary and storing the retinal map in the database, receiving, at a display controller, an image from a camera or cameras associated with the patient, applying corrections to the image based on the retinal map, and responsively generating a corrected image. Further, the method includes the steps of receiving, at a display unit, the corrected image and presenting the corrected image to the eye of the patient.

In still other embodiments, one or more non-transitory computer-readable storage media, have computer-executable instructions embodied thereon. When executed by at least one processor, the computer-executable instructions cause the at least one processor to establish, by a model controller, a visual model associated with a patient and storing the visual model in the database. The visual model includes data related to a quality of the patient's vision. A boundary is established as a function of data associated with the visual model, the boundary being indicative of an area to be corrected within the patient's vision. A retinal map is established as a function of the boundary. An image from a camera or cameras associated with the patient is received at a display controller. Corrections are applied to the image based on the retinal map, and a corrected image is generated. The corrected image is presented to the eye of the patient.

BRIEF DESCRIPTION OF THE FIGURES

Other advantages of the present disclosure will be readily appreciated, as the same becomes better understood by reference to the following detailed description when considered in connection with the accompanying drawings wherein.

Non-limiting and non-exhaustive embodiments of the present invention are described with reference to the following figures, wherein like reference numerals refer to like parts throughout the various views, unless otherwise specified.

Figure 1:
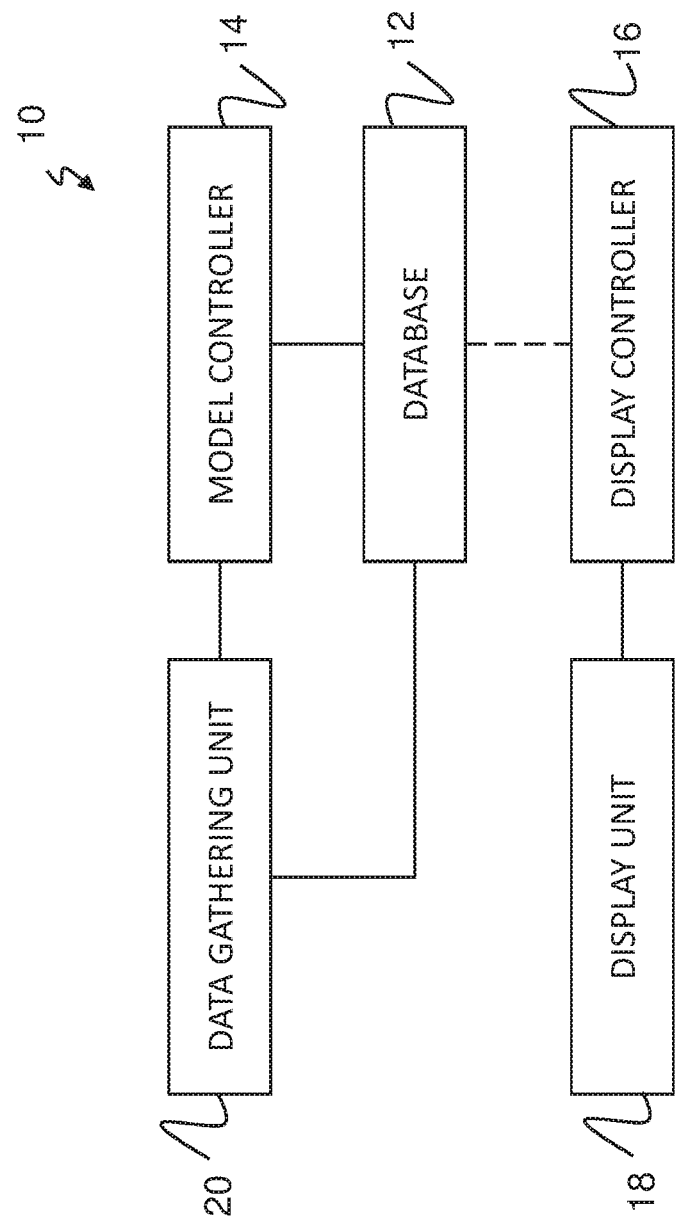
FIG. 1 is a block diagram of a system to augment a patient's vision, according to an embodiment of the present invention.

Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention.

DETAILED DESCRIPTION

In the following description, numerous specific details are set forth in order to provide a thorough understanding of the present invention. It will be apparent, however, to one having ordinary skill in the art that the specific detail need not be employed to practice the present invention. In other instances, well-known materials or methods have not been described in detail in order to avoid obscuring the present invention.

Reference throughout this specification to "one embodiment", "an embodiment", "one example", or "an example" means that a particular feature, structure or characteristic described in connection with the embodiment or example is included in at least one embodiment of the present invention. Thus, appearances of the phrases "in one embodiment", "in an embodiment", "one example", or "an example" in various places throughout this specification are not necessarily all referring to the same embodiment or example. Furthermore, the particular features, structures or characteristics may be combined in any suitable combinations and/or sub-combinations in one or more embodiments or examples. In addition, it is appreciated that the figures provided herewith are for explanation purposes to persons ordinarily skilled in the art, and that the drawings are not necessarily drawn to scale.

Embodiments in accordance with the present invention may be embodied as an apparatus, method, or computer program product. Accordingly, the present invention may take the form of an entirely hardware embodiment, an entirely software embodiment (including firmware, resident software, micro-code, etc.), or an embodiment combining software and hardware aspects that may all generally be referred to herein as a "unit", "module" or "system." Furthermore, the present invention may take the form of a computer program product embodied in any tangible media of expression having computer-usable program code embodied in the media.

Any combination of one or more computer-usable or computer-readable media (or medium) may be utilized. For example, a computer-readable media may include one or more of a portable computer diskette, a hard disk, a random access memory (RAM) device, a read-only memory (ROM) device, an erasable programmable read-only memory (EPROM or Flash memory) device, a portable compact disc read-only memory (CDROM), an optical storage device, and a magnetic storage device. Computer program code for carrying out operations of the present invention may be written in any combination of one or more programming languages.

The flowchart and block diagrams in the flow diagrams illustrate the architecture, functionality, and operation of possible implementations of systems, methods, and computer program products according to various embodiments of the present invention. In this regard, each block in the flowchart or block diagrams may represent a module, segment, or portion of code, which comprises one or more executable instructions for implementing the specified logical function(s). It will also be noted that each block of the block diagrams and/or flowchart illustrations, and combinations of blocks in the block diagrams and/or flowchart illustrations, may be implemented by special purpose hardware-based systems that perform the specified functions or acts, or combinations of special purpose hardware and computer instructions. These computer program instructions may also be stored in a computer-readable media that can direct a computer or other programmable data processing apparatus to function in a particular manner, such that the instructions stored in the computer-readable media produce an article of manufacture, including instruction means which implement the function/act specified in the flowchart and/or block diagram block or blocks.

Several (or different) elements discussed below, and/or claimed, are described as being "coupled", "in communication with", or "configured to be in communication with". This terminology is intended to be non-limiting, and where appropriate, be interpreted to include without limitation, wired and wireless communication using any one or a plurality of a suitable protocols, as well as communication methods that are constantly maintained, are made on a periodic basis, and/or made or initiated on an as needed basis.

The disclosure particularly describes a system 10, method M10 and computer program instructions stored in media, that augment the sight of an individual or patient whose sight has been damaged or is otherwise defective. In general, the present invention provides techniques that may be implemented in systems, methods, and/or computer-executable instructions that (1) map the defective areas of the patient's sight, (2) establish one or more boundaries that delineate between the effective and defective areas of the patient's eye(s), (3) capture an image (or series of images) using a camera associated with the patient, (4) map the capture image (or series of images) and generate a corrected image (or series of images), and (5) present the correct image(s) to the patient's eye(s).

With reference to FIG. 1, an exemplary system 10, according to one embodiment of the present invention, is illustrated. The system 10 includes a database 12, a model controller 14, a display controller 16, and a display unit 18. As will be discussed in more detail below, a data gathering unit 20 is used to gather data that may be used to develop a visual model of the patient's eyesight. The data used to establish the visual model, the visual model and other data is stored in the database 12. Since the peripheral receptors, in the macular degeneration case, in the retina are usually still functioning, the present invention stretches, skews and/or otherwise manipulates the image(s) presented to the eye(s) of the patient to avoid the macula or the damaged portions of the macula. Thus, the entire image is presented to, or onto, the functioning retinal receptors. As explained in more detail below, the present invention creates a distortion map of the image and displays it, or projects it onto the periphery of the eye(s), while avoiding the (damaged portion of the) macula. The distorted image is presented to, projected onto, the eye using (high definition) goggles, glasses, a "smart" contact lens, or a photon projection (using a virtual retina display) of the image directly onto the periphery of the eye.

In general, the model controller 14 is coupled to the database 12 and is configured to establish the visual model associated with a patient and to store the visual model in the database. The visual model includes data related to a quality of the patient's vision. The model controller 14 is further configured to establish a boundary as a function of data associated with the visual model. This process is discussed in further detail below. The boundary is indicative of an area to be corrected within the patient's vision. The model controller is further configured to establish a retinal map as a function of the boundary and to store the retinal map in the database.

The display controller 16 is configured to receive and to store the retinal map. The display controller 16 is further configured to receive an image (or series of images) from a camera, such as a video camera, (see below) associated with the patient and to apply corrections to the image(s) based on the retinal map and responsively generate corrected image(s).

In one aspect of the present invention, one or more retinal maps may be generated. The retinal map may be associated with predefined settings, for examples, day time, night time, reading, etc. The correct retinal map may be automatically selected for specific conditions and/or may be user selectable to fit changing conditions.

The display unit 18 is coupled to the display controller 16 and is configured to receive the corrected image(s) and to present the corrected image(s) to the eye of the patient. It should be noted that the present invention may be configured to present corrected video, as a series of images, to the eye of the patient.

In general, the model controller 14 and database 12 may be an embodiment, in a computer, specific or specifically designed hardware or apparatus, server, or servers operating independently, or in a networked environment. The data gathering unit 20 (described in further detail below) may be linked, at least temporarily, or may be data transferred over a network, electronically, or through a physical media.

In one aspect of the present invention, the retinal map may be established automatically and adjusted (with or without the patient's input) at or by the model controller and then transferred electronically to the display controller.

In another aspect of the present invention, the model controller 14 may establish a plurality of retinal maps that vary in either the parameters used to generate the retinal map and/or the method used to generate the retinal map. The plurality of retinal maps may be stored at the display controller 16. The patient may then cycle through the retinal maps and select, for use, one of the retinal maps that works best. For instance, a particular retinal map may work best for the instant conditions. Thus, the patient may select a retinal that works best for the conditions which currently exist.

As discussed more fully below, the display controller 16 and the display unit 18 may be embodied in a head mounted display, goggles, or glasses that are mounted to, or worn by the patient. Alternatively, the display controller 16 and display unit 18 may be embodied in a unit that is separated from, i.e., not worn by, the patient. One or more sensors (not shown) may be utilized to find the location and distance of the patient relative to the display unit 18 such that the image may be displayed properly.

Each eye of the patient is different. For instance, one eye of the patient may have a specific defect (having a specific shape, size and location), while the other eye of the patient may not have a defect or may have a defect having a different shape and size. Thus, each eye of the patient will generally be mapped and a respective visual model of each eye established. A boundary of the defect of each eye will be generated and an associated retinal map generated. In one embodiment, separate cameras will generate a separate set of images for each eye and the display controller 16 will generate a respective series of images to be presented to each eye.

Figure 2:
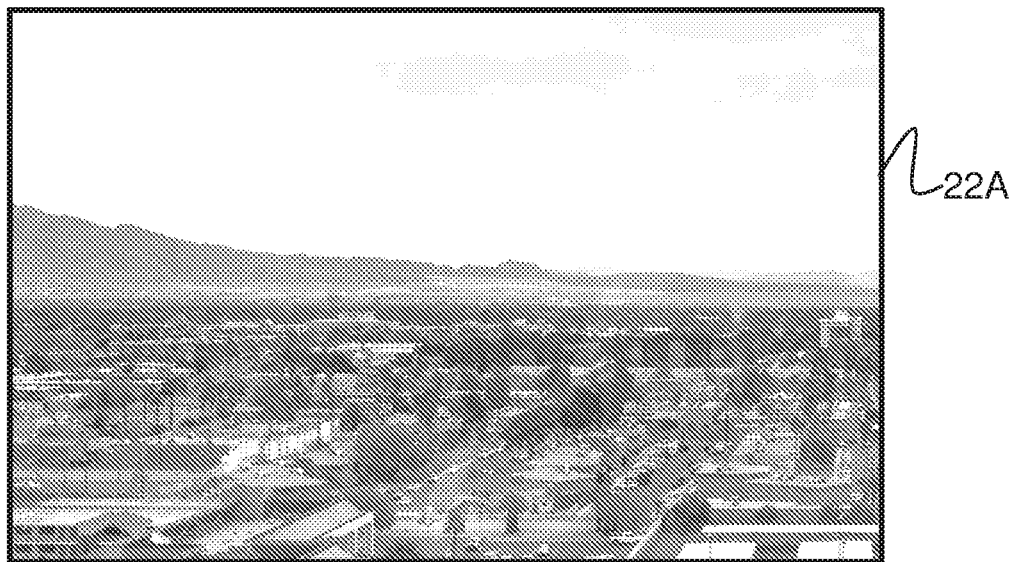
FIG. 2 is a diagrammatic illustration of a patient's vision without a defect.
Figure 3:
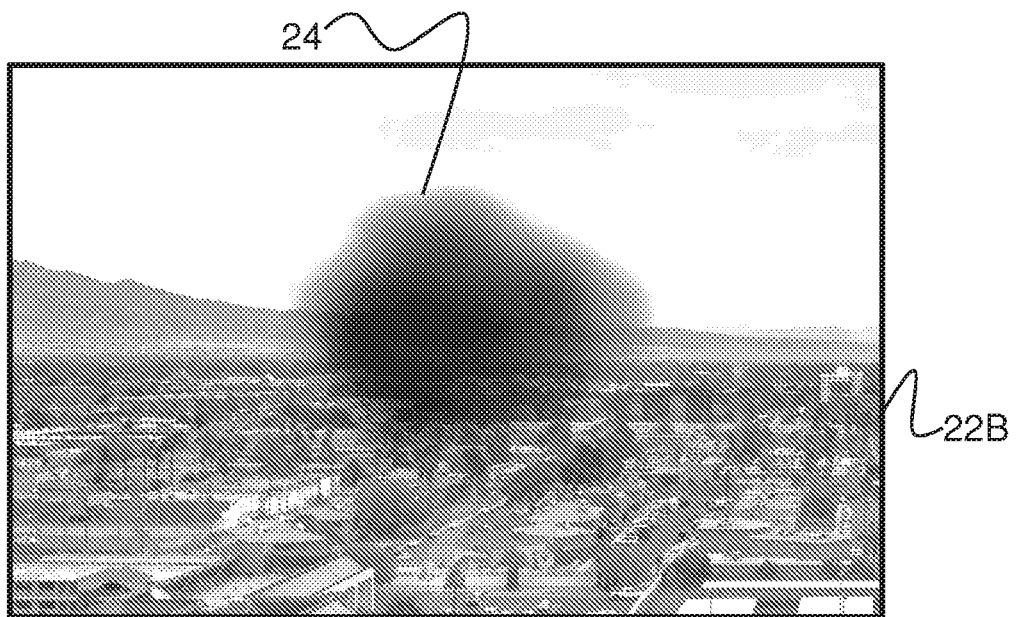
FIG. 3 is a diagrammatic illustration of a patient's vision with a defect.

With reference to FIG. 2, a graphic 22A representing the vision of a patient's eye without a defect is shown for purposes of comparison. With reference to FIG. 3, a graphic 22B representing the vision of a patient's eye with a defect is shown. The defect is represented by the dark shape 24 shown in the center of the graphic 22B.

In one aspect of the present invention, the visual model may be established using the data gathering unit 20. The data gathering unit 20 may include at least one of (1) a field of vision ophthalmological instrument, (2) a portable mobile field of vision test apparatus, and (3) a computer based system. The process of gathering data using the data gathering unit 20 is discussed in more detail below.

Figure 4A:
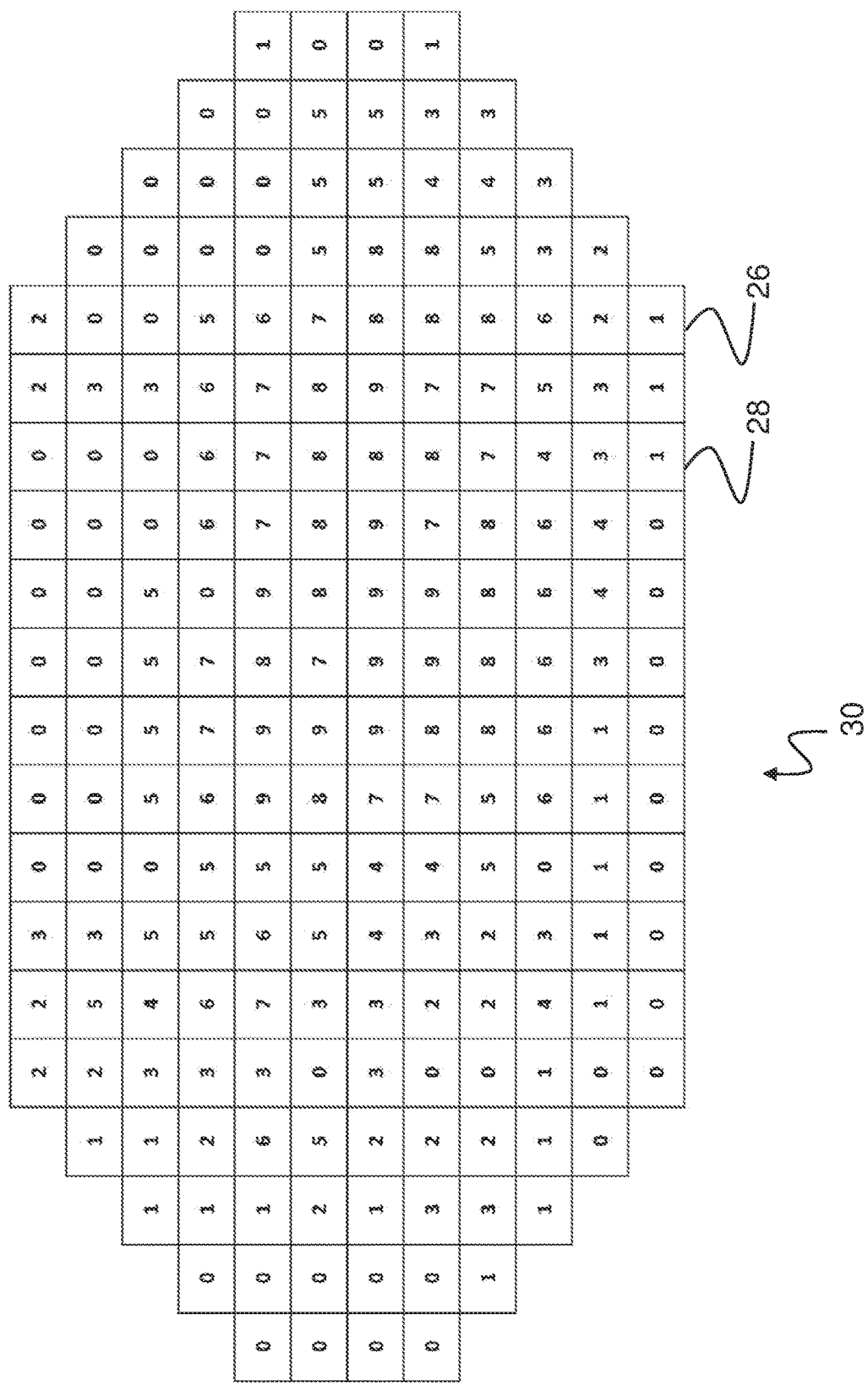
FIG. 4A is an illustration of a sample visual model, according to an embodiment of the present invention.

With reference to FIG. 4A, a simplified example of field of vision (FOV) data 26 is shown. The FOV data 26 is used to create the visual model. The FOV data 26 includes a plurality of cells 28 arranged in a grid 30. Each cell 28 has an associated value associated with the quality of the patient's vision. The values may be based on an absolute or representative scale that is indicative of the quality of vision. Alternatively, the values may be a deviation from a standard value, or a value of an associated cell. For purposes of explanation, in the exemplary FOV data 26 of FIG. 4A, the values in the grid utilize a scale of 0-9, where 0 represents no defect, 9 represents a defect and the values 1-8 represent a quality of vision between 0 and 9. It should be noted that a scale of 0-9 is for discussion purposes only. The scale utilized may be any suitable scale, for example, 0-99, 0-255, −30 to 30, or any suitable scale. Furthermore, the illustrated grid having 12 rows and 20 columns. The shape of the grid may be used to approximate the shape of an eye and may be different between the left and the right eye. However, the size and the shape of the grid may be based on a 12×20 grid, however, any size grid may be utilized. The size of the grid may be dependent upon the data gathering process, or data gathering unit 20 and/or the display unit 18. In another embodiment, the FOV data may be represented by a contour, polygon or morphological operator.

Figure 4B:
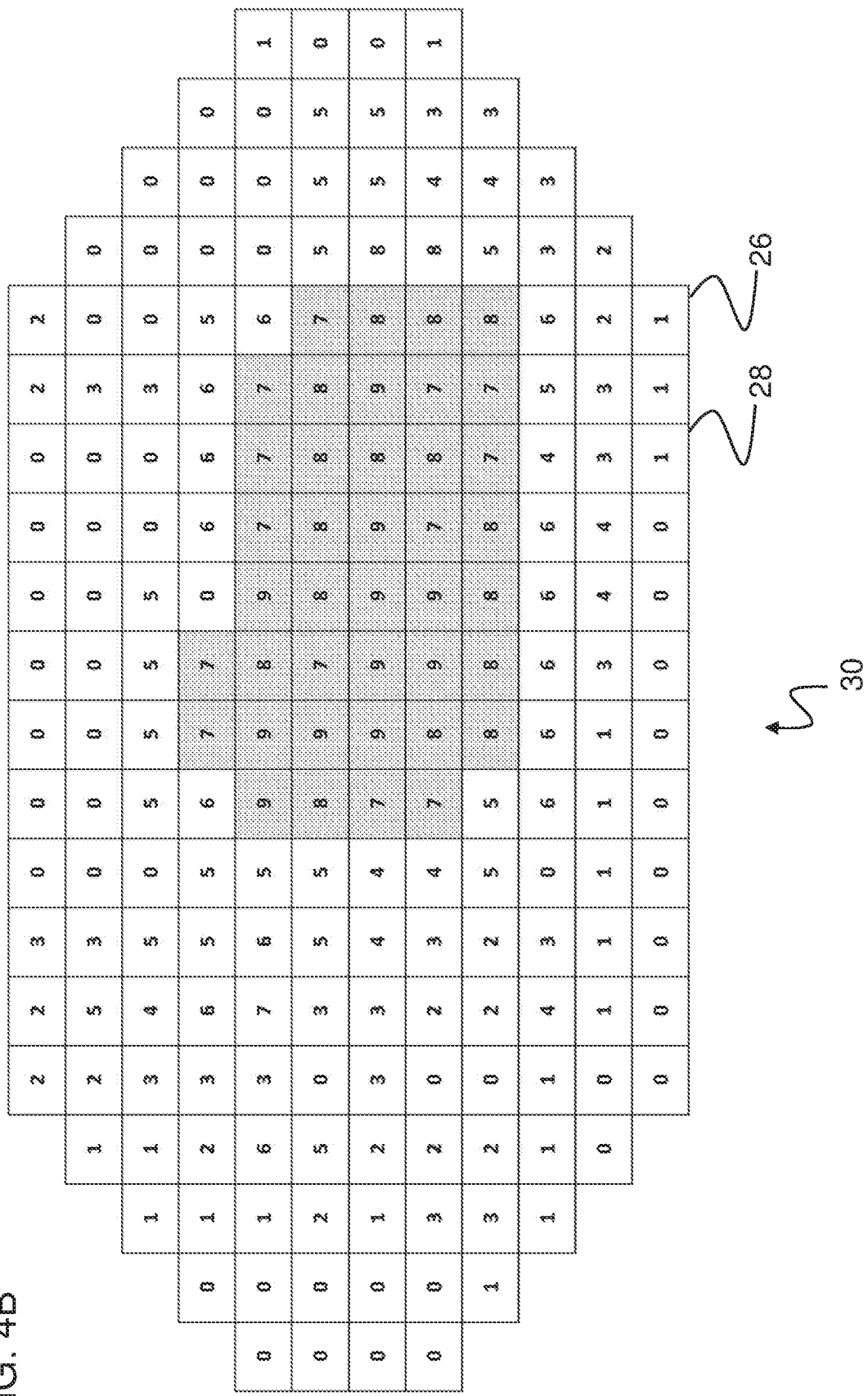
FIG. 4B is an alternative view of the sample visual model of FIG. 4B.

The boundary may be established as a function of the values associated with the cells in the grid. In one embodiment, the values in the grid values are compared with a threshold to establish the boundary. For example, in the above example, the threshold may be set to 7. Thus, any cell 28 having a value of 7 or greater is within the boundary and any cell 28 having a value of 0 is outside of the boundary. A modified view of the FOV data 26 is shown in FIG. 4B, in which the cells 28 meeting the above threshold are highlighted.

Alternatively, the FOV data 26 could be used to create a contour. The visual model emerges from interpreting the raw data and is not necessarily a point-by-point transformation of the raw data.

Figure 5:
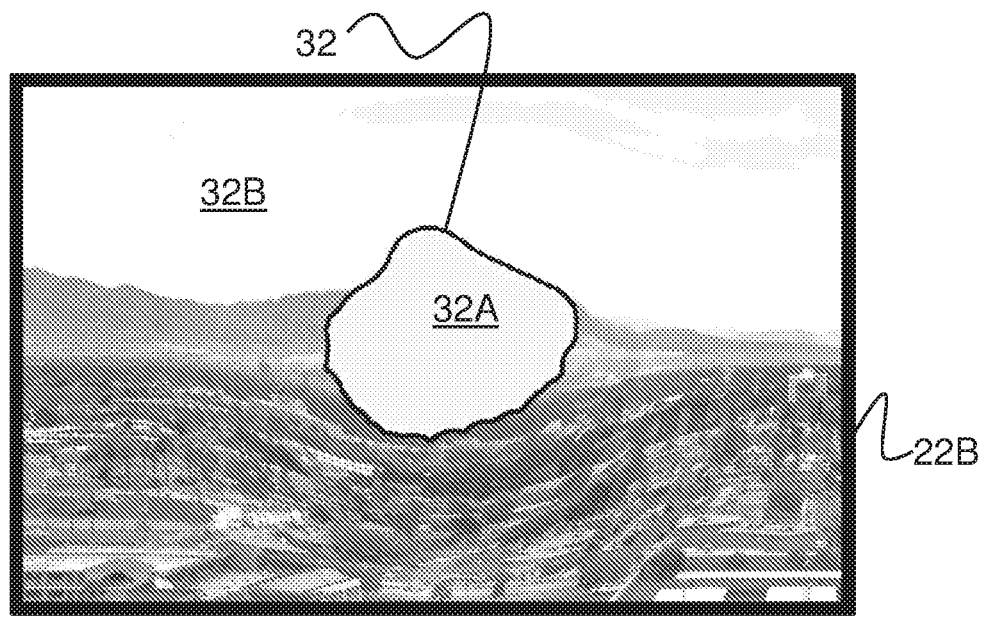
FIG. 5 is an illustration of a complex boundary, according to an embodiment of the present invention.

With reference to FIG. 5, an exemplary boundary 32 is shown. The area 32A is within the boundary 32 and the area 32B is outside of the boundary.

In one aspect of the present invention, the data comprising the visual model may be filtered or transformed to eliminate noise or other undesirable effects within the data prior to the boundary (or boundaries) being established. This process may be performed automatically using a set of predefined operations or may be performed under the control of an operator of the model controller 14. For instance, the data may be filtered using one or more morphological transformations. Possible morphological transformations or operations may include, but are not limited to: erosion, dilation, opening, morphological gradient, top hat, and/or black hat. An initial boundary may be established using pre-filtered data and a secondary boundary may be established after the data has been filtered or transformed. The initial and secondary boundary may be compared automatically or by the operator to optimize the boundary used. Alternatively, Boolean operations may be used to filter the visual model and/or combining boundaries.

In one aspect of the present invention, the threshold is adjustable, either at the model controller 14 or at the display controller 16. If performed at the model controller 14, this would provide control to the operator. In adjusting the threshold, the operator could optimize the boundary. If performed at the display controller 16, control would be provided to the patient. This would allow the patient to adjust the boundary to optimize the boundary for current conditions.

In another aspect of the present invention, the model controller 14, in establishing the boundary, is configured to establish a first boundary and a second boundary. The model controller 14 is configured to evaluate the first and second boundaries and to responsively establish a final boundary. The first and second boundaries may be joined into a single boundary (incorporating at least a portion of each of the first and second boundary). Alternatively, one or both of the boundaries may be eliminated if the boundary does not meet a set of predefined criteria. For instance, if one of the boundaries does not have a predetermined height, width, or total area, then it may be eliminated.

Figure 6:
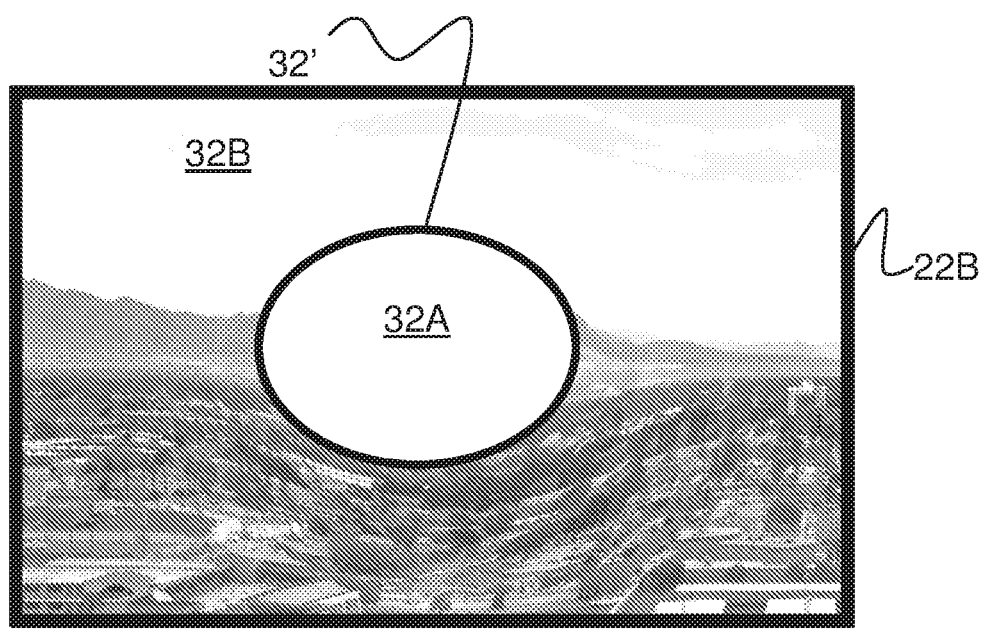
FIG. 6 is an illustration of a simple boundary comprised from one of a plurality of predefined shapes.

In another embodiment of the present invention, the boundary 32 may be adjusted or replaced with a simpler form (boundary 32', see FIG. 6). For instance, the boundary 32 may be replaced with a boundary established as a function of one or more predesigned shapes and the visual model. The model controller 14 may utilize a set of pre-defined set of shapes, for example, rectangles, triangles, ovals that are sized to include the affected area. The model controller 14 may select one or more shapes automatically, or the process may be performed by, or with the assistance of, the operator.

Figure 7:
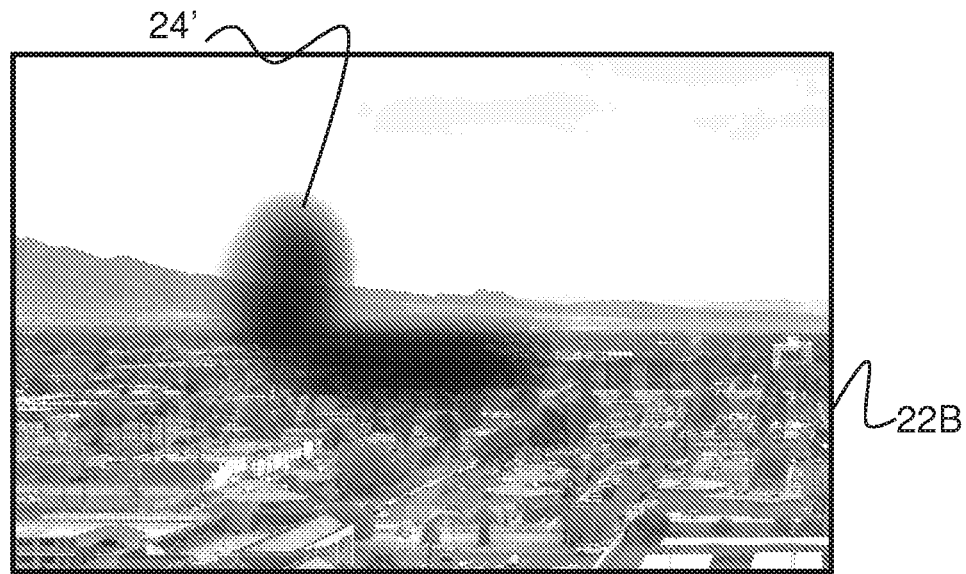
FIG. 7 is an illustration of a patient's vision with a more complex defect.
Figure 8:
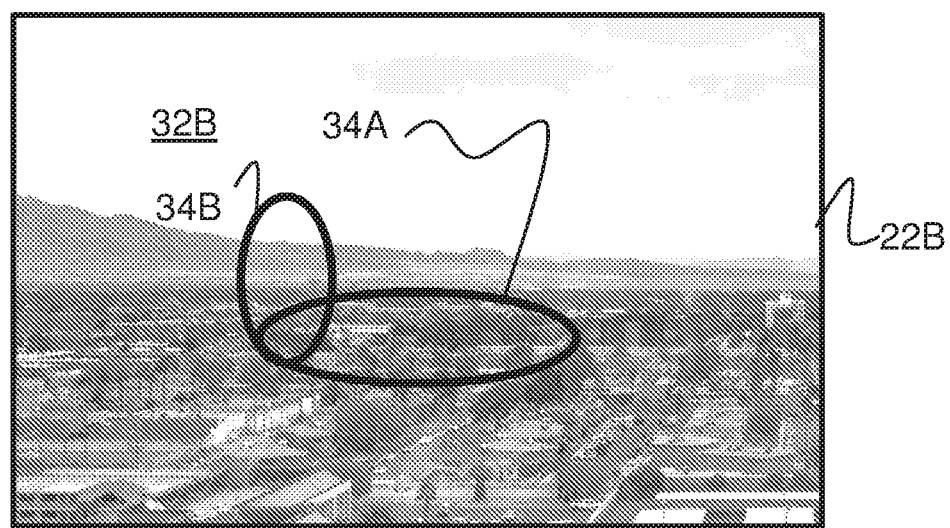
FIG. 8 is an illustration of a boundary associated with the illustration of FIG. 7.

With reference to FIG. 7, the shape of the defect or damaged area 24' may be more complex. A complex boundary may be established using the threshold process identified above, or by some other method. Alternatively, the initial boundary may be replaced automatically, or with operator input using one or more of the predefined shapes, sized to cover the defect. In the example of FIG. 8, two shapes 34A, 34B are used. The boundary may be formed by the outer edge of the joined shapes.

Figure 9:
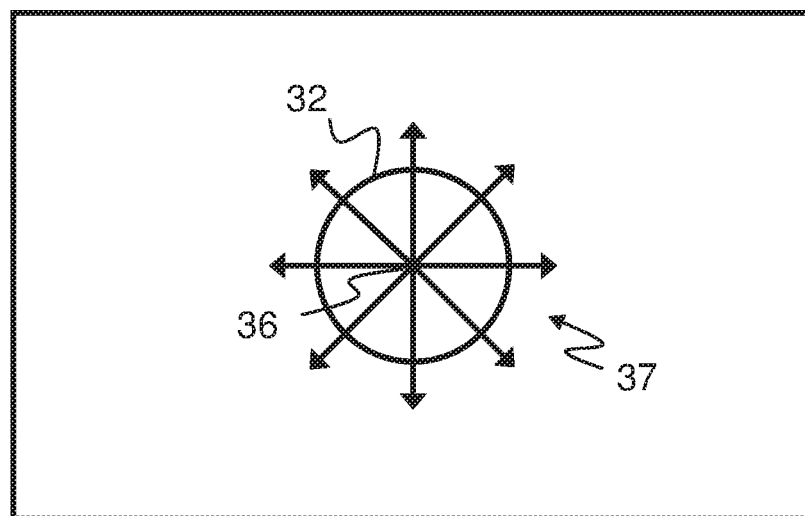
FIG. 9 is a diagrammatic illustration used in establishing a retinal map, according to an embodiment of the present invention.
Figure 10:
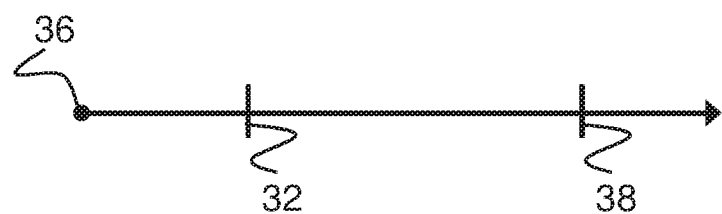
FIG. 10 is a diagrammatic illustration used in establishing a retinal map, according to an embodiment of the present invention.

With reference to FIGS. 9 and 10, in one aspect of the present invention, the image data inside the boundary 32 is shifted outside of the boundary 32. In the example shown in FIG. 9, first a center point 36 is established. The center point 36 may be an actual center of the boundary if the shape of the boundary is regular, or it may be defined by finding or estimating the center of the shape defined by the boundary. In one embodiment, image data along a plurality of rays 37 starting at the center point and extending outward is shifted outside of the boundary. It should be noted that in the above examples, the areas inside the boundary or boundaries are defective. However, in some situations, for example, where peripheral vision is affected, the area inside a boundary may be associated with good vision and the areas outside of a boundary may be associated with poor vision.

In one embodiment, the retinal map includes a series of data points which overlay the digital model. The data points are laid out in a grid in a regular pattern. Each data point is defined by a set of X, Y coordinates relative to the image data. As explained in detail below, each data point is assigned a set of coordinate transformation values ($\Delta X$, $\Delta Y$), which is used to transform the image data. Each data point lies on a single ray which extends outward from the center point 36. For each data point, the associated ray is found and a set of coordinate transformation values ($\Delta X$, $\Delta Y$) are established based on a set of predetermined rules. The coordinate transformation values ($\Delta X$, $\Delta Y$) are used as coefficient values in the transformation equations below.

In one embodiment, visual information in the image from the camera is radially shifted from a central point. For instance, in one embodiment the image data from the center point 36 to the edge of the image 38 is compressed (in the corrected image) from the boundary 32 to the edge of the image 38. Thus, the coordinate transformation values (ΔX, ΔY) for any data point lying on the ray may be calculated based on the length of the distance from the center point 36 to the boundary 32, and the length from the center point 36 to the respective edge of the image 38.

Figure 11:
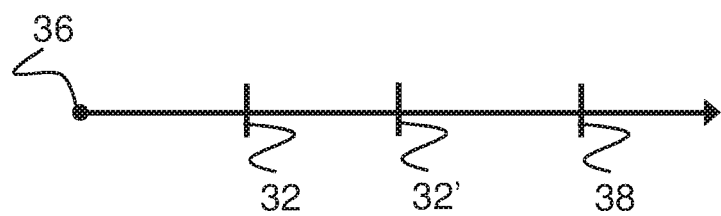
FIG. 11 is a diagrammatic illustration used in establishing a retinal map, according to another embodiment of the present invention.

In an alternative embodiment, the coordinate transformation value (ΔX, ΔY) is calculated such that the visual information is disproportionally shifted from the center point. For example, with respect to FIG. 11, visual information from the center point 36 to the boundary 32 may be shifted to a segment of the ray defined by the boundary 32 and a point 32'. The length between the boundary 32 and point 32' may be equal to or different than the length between the center point and the boundary 32. In this embodiment, the visual information between the boundary and the edge of the image 38 may be compressed between point 32' and the edge of the image 38. Not only can the visual information be shifted out towards the periphery but can also be accomplished in reverse and the visual information can be shifted inward as well.

Once coordinate transformation values are established, the retinal map is stored in the database 12 and transferred to the display controller 16. In use, the retinal map is then used to transform the image(s) received from the camera and generate the corrected image(s). The corrected image(s) may then be displayed in real-time via the display unit 18.

In one aspect of the present invention, the visual information is transformed (or moved) at each data point. The visual information between the data points may be transformed using a spline function, e.g., a B spline function, to interpolate the visual information between the data points. In another aspect of the invention, the pixels relating to the data portion of the image which is moved are reduced to smaller pixels, such that the moved pixels and the preexisting pixels occupy the same space on the display. Or, the removed and replaced pixels may be interlaced into a video frame consisting of two sub-fields taken in sequence, each sequentially scanned at odd then even lines of the image sensor.

The display controller, in generating the corrected image, shifts visual information within the corrected image in a first area inside the boundary to a second area outside of the boundary as a function of the series of data points. The coordinate transformation values are used to shift image data that exists inside the boundary to an area outside of the boundary. In the above example, the second area is defined as any area in the image that is outside of the boundary.

Figure 4C:
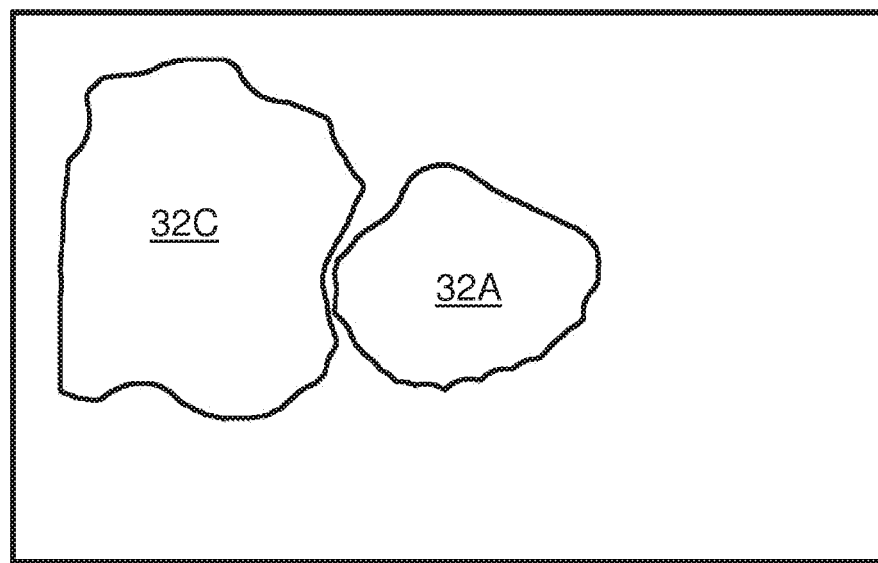
FIG. 4C is an illustration of first and second boundaries, according to an embodiment of the present invention.
Figure 4D:
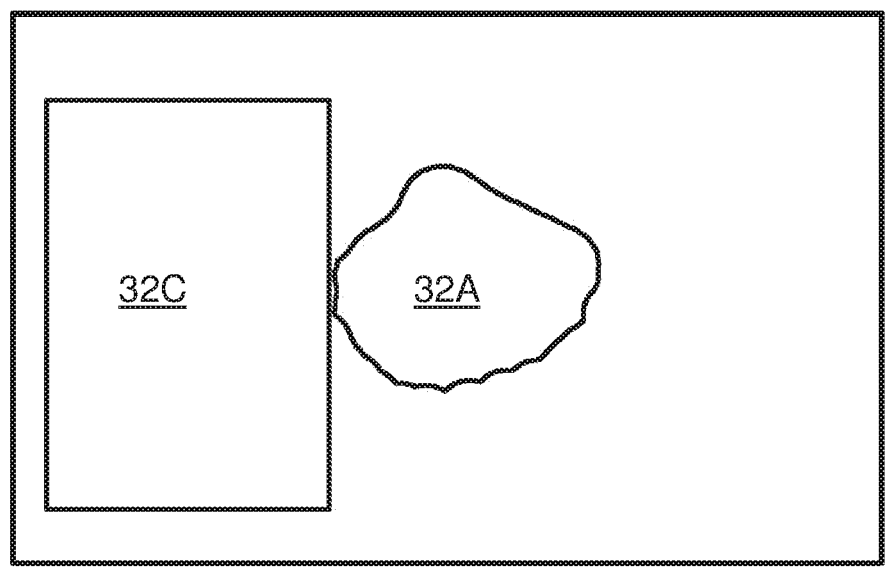
FIG. 4D is an illustration of first and second boundaries, according to another embodiment of the present invention.

In another embodiment, the second area may be defined based on the data in the visual model. For example, a second boundary may be established as a function of the data in the visual model. In one example, the second boundary may be established based on the visual model that meets predefined criteria. For example, an area within the visual model may be established cells 28 in the grid 30 that have a value that meets predefined criteria. In the example above, for instance, the second boundary may encompass an area of the grid 30 in which the cells 28 have a value of 3 (or some other threshold) or less. In this embodiment, the information inside the first boundary 32 is shifted (proportionally or disproportionally) into the area defined by the second boundary. Examples of an area defined by a first area 32A and an area defined by a second area 32C are shown in FIGS. 4C and 4D. In both examples, visual information in one of the areas 32A or 32C may be shifted towards or into the other one of the areas 32A, 32C. In the illustrated examples, the second boundary in FIG. 4C has been replaced with a simpler shape/form in FIG. 4D.

In one aspect of the present invention, the display controller 16 and the display unit 18 may be implemented in a suitable user wearable device, such as smart glasses or head mounted displays (HMDs). Such devices are available and/or or in development from Lumus, Ostherhut Design, Meta, Magic Leap, Microsoft, Oculus, Google, Sony, Epson, Immy and other vendors. In all cases, these hardware wearable platforms all contain wearable glasses that contain one or two forward mounted cameras, and onboard microprocessor, display technologies for viewing by the eye. Furthermore, these are usually battery powered, as well as able to plug into a PC in order to upload information via a USB cable etc. and/or for charging. This may also include HUD (Heads Up Displays), for example, the offering from Meta can be worn over a patient's existing glasses with prescription lenses 62 in order to facilitate moving between the two modes of normal vision and the augmented IDM (Image Distortion Map) vision. These wearable HMDs can include different display technology such as separate LCD, LED, OLED type of displays. In general, these devices may include an embedded display on the actual lenses of the glasses that overlay the image to view the augmented display in conjunction with the outside world. Alternatively, a virtual retina display maybe used to project photons directly onto the retina, or a "smart" contact lens can project the image that is worn on the eye. Any suitable method or device to present the correction image or images to or onto the eye(s) may be used. Alternatively, the image or images presented to the patient may be otherwise opaque such that the outside world is not visible.

Figure 12:
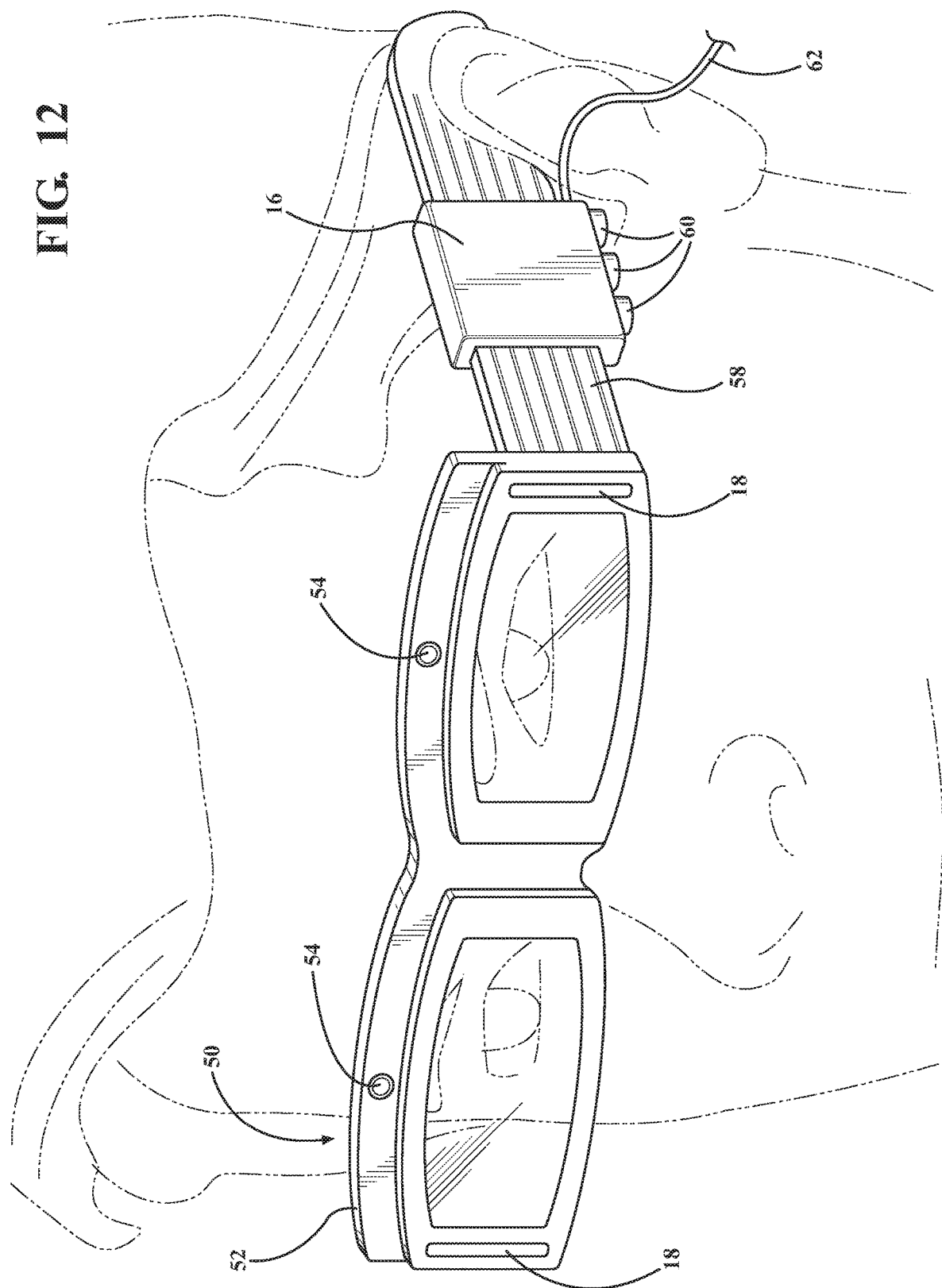
FIG. 12 is a diagrammatic illustration of a head mounted display unit, according to an embodiment of the present invention.
Figure 13:
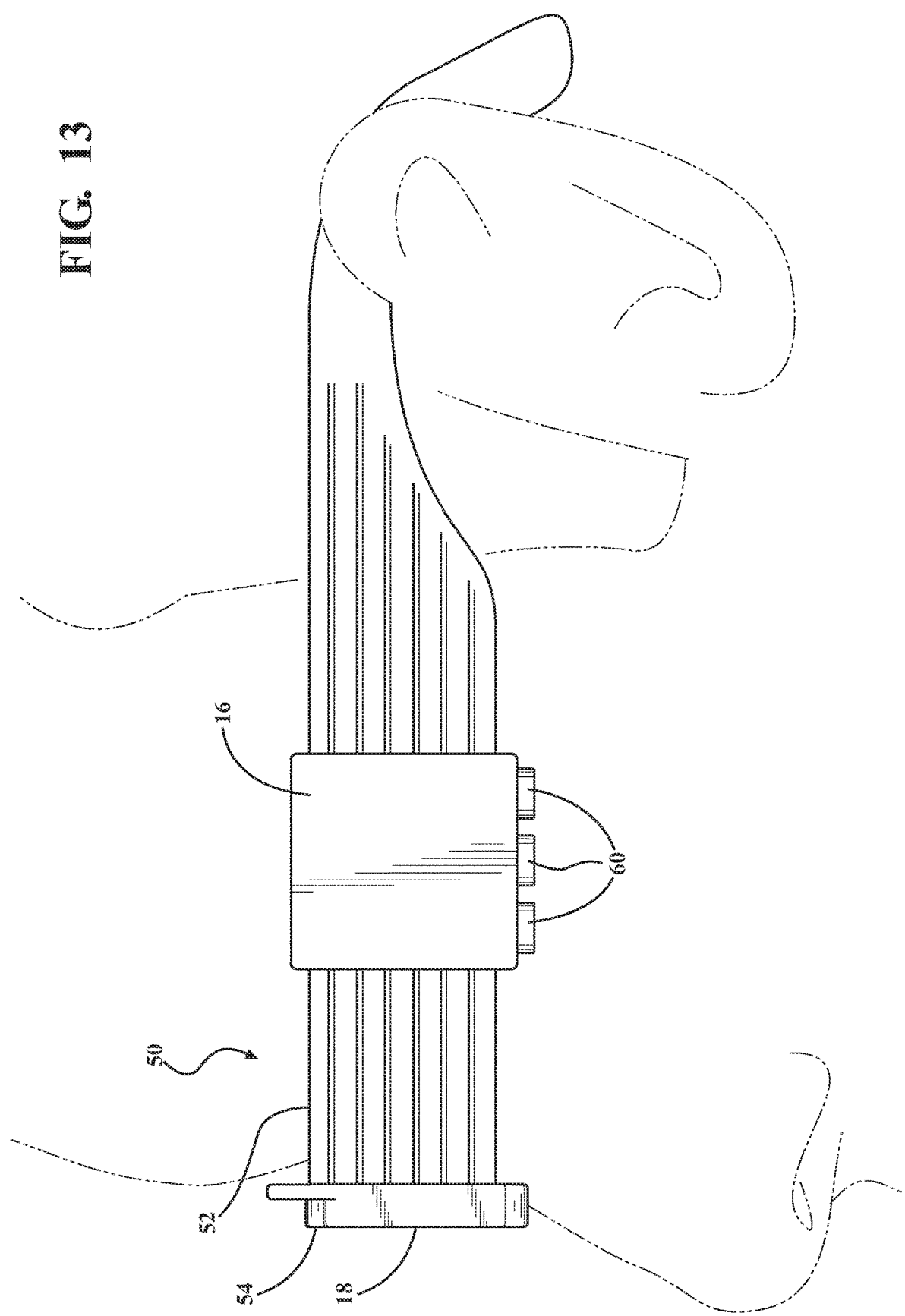
FIG. 13 is a second diagrammatic illustration of the head mounted display unit of FIG. 12.

With reference to FIGS. 12 and 13, in one embodiment, the display controller 16 and the display unit 18 are embodied in an exemplary head mountable display (HMD) device 50 that is worn by the patient. In the illustrated embodiment, the HMD device 50 includes a set of wearable glasses 52 that contains one or two forward mounted cameras 54. The display controller 16 may be mounted to an HMD frame 58 and include an onboard microprocessor. The display unit 18 includes a suitable display technology for viewing by the eye. One or more input or control buttons may be provided that work in conjunction with suitable menus, and software controls display on the display unit 18 to allow the patient/user to change options. The HMD device 50 may be battery powered and may include a USB cable or suitable port 62 to connect to, e.g., a computer to transfer data and software and/or for charging the battery.

Figure 14:
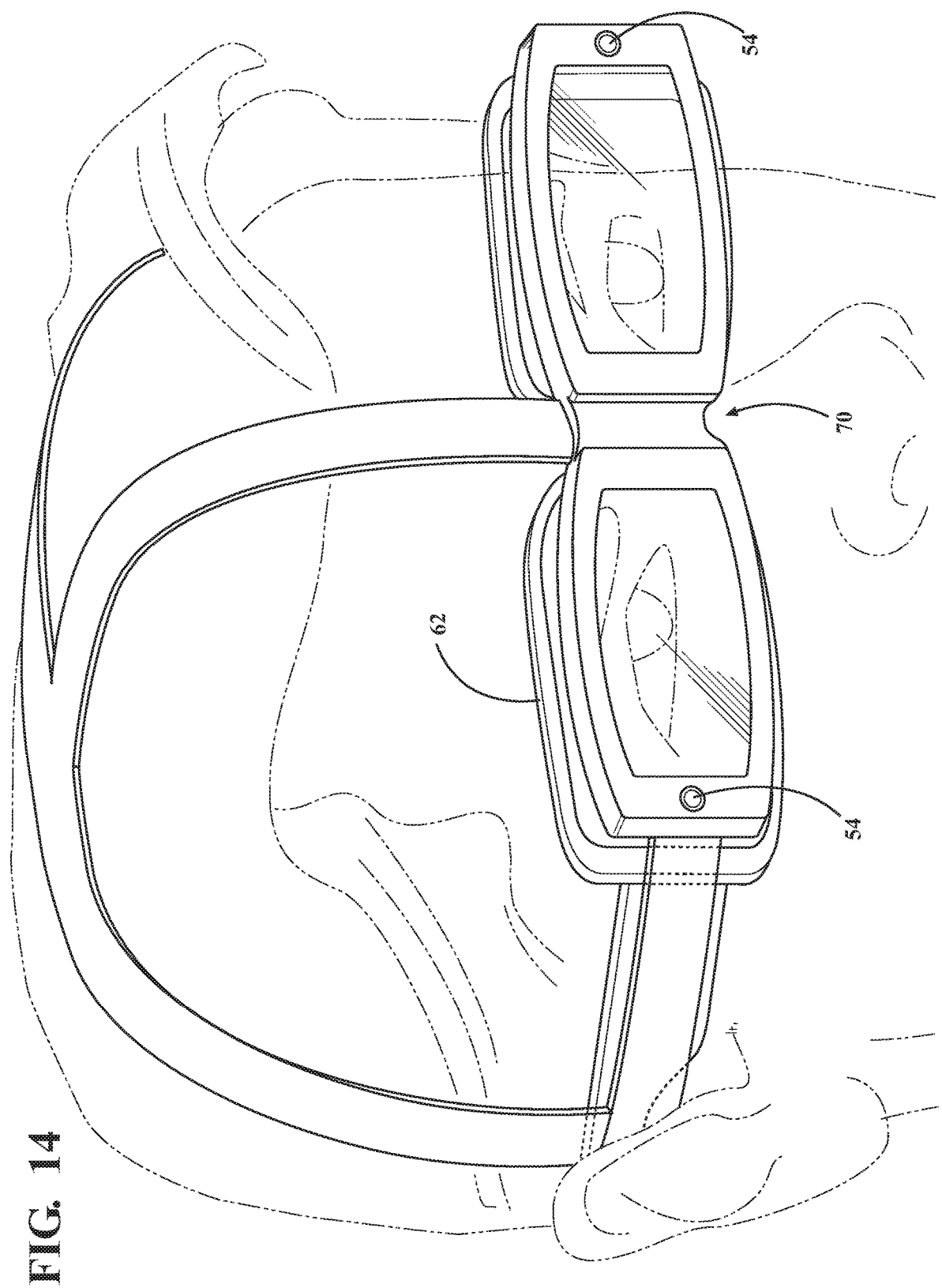
FIG. 14 is a diagrammatic illustration of a heads up display unit, according to an embodiment of the present invention.

With reference to FIG. 14, the display controller 16 and the display unit 18 may also be embodied in a Heads Up Displays (HUD) display device 60, for example, the offering from Meta, that can be worn over a patient's existing glasses with prescription lenses in order to facilitate moving between the two modes of normal vision and augmented IMD vision. The HUD display device 60 are head mountable and may include different display technology such as separate LCD or LED type of display. The HUD display device 60 may embed a display on the actual lenses of the glasses themselves that overlay the image to view the augmented display in conjunction with the outside world.

Figure 15:
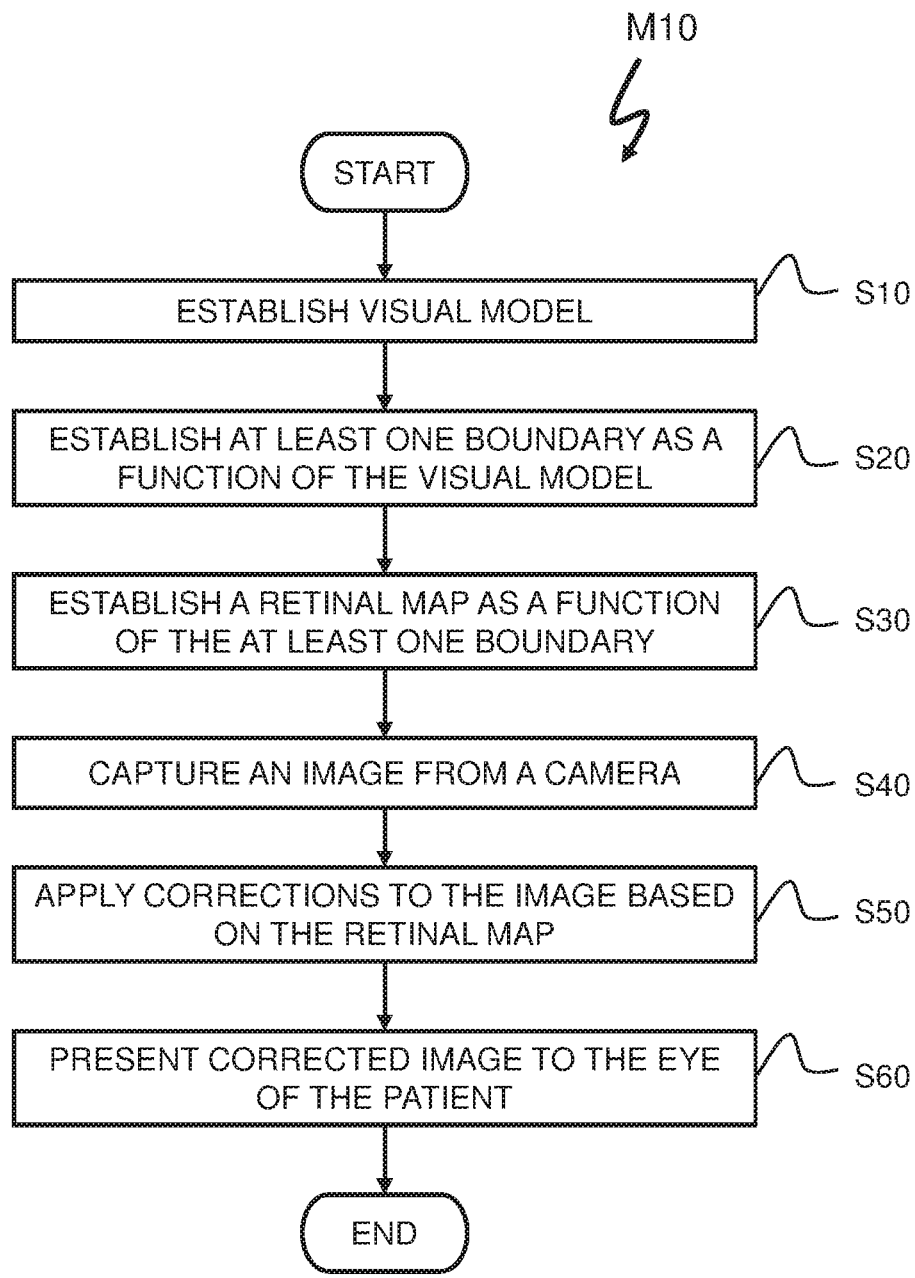
FIG. 15 is a flow diagram of a method for augmenting the vision of a patient, according to an embodiment of the present invention.
Figure 16:
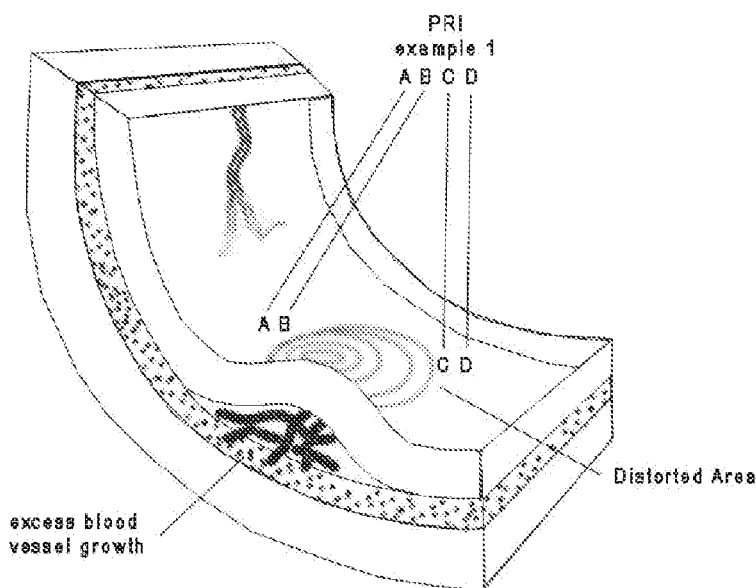
FIG. 16 is a graphical illustration of a first example of a manipulation of prescribed retinal interface, according to an embodiment of the present invention.
Figure 17:
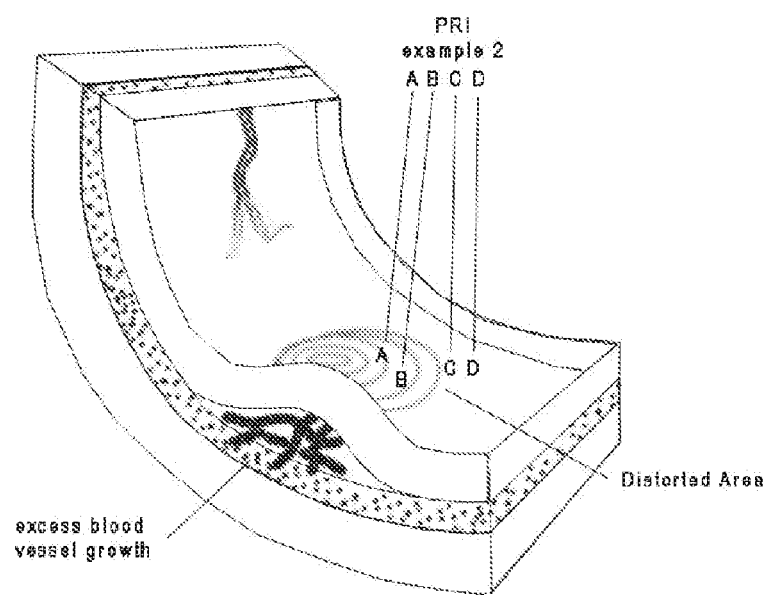
FIG. 17 is a graphical illustration of a second example of a manipulation of prescribed retinal interface, according to an embodiment of the present invention.

With reference to FIG. 15, in another aspect of the present invention, a method M10 according to one embodiment of the present invention is provided. In a first step S10, a visual model associated with a patient is established, by the model controller 14 and stored in the database 12. The visual model includes data related to a quality of the patient's vision. In a second step S20, at least one boundary is established, by the model controller 14, as a function of data associated with the visual model. At least one boundary is indicative of an area to be corrected within the patient's vision. In a third step S30, the model controller 14 establishes a retinal map as a function of the boundary and stores the retinal map in the database 12. The database may be incorporated into a semiconductor chip, which may also be existing space in a camera chip.

In a fourth step S40, an image from a camera associated with the patient is received by a display controller 16. Corrections to the image based on the retinal map are applied to the image and a corrected image is generated in a fifth step S50. In a sixth step S60, the corrected image is received at the display unit 18 and presented to the eye of the patient.

The system 10 and method M10, in general, remap portions of the image(s) captured by the camera(s) which would be viewed by the effected portions of the patient's eye(s) to the periphery or unaffected portions of the patient's vision, or alternatively to another portion of the patient's retina. With this mapping correctly, executed the patient's brain adapts quickly and effective central (or periphery) vision is mimicked. This is accomplished with the forward-looking cameras as the sensor that captures the real world image. The system 10 and method M10 of the present invention shift the pixels to form a corrected image or series of images which are displayed on the micro-displays on a head mounted device, such as readily available augmented reality and virtual reality glasses. This process is all non-invasive and depends only on the processor in the glasses, the remapping software, and the patient's brain processing power through direct observation of the micro-display. The display device utilized may be implemented in head mounted devices, suitable examples of which are these offered by companies such as Sony, Epson, Facebook, Google, etc., utilize a variety of display technologies, such as LED, LCD, OLED, Photon Retinal Display, Virtual Retinal Displays, and Heads Up Displays.

Field of Vision Mapping

In order to correctly enable the pixel remapping technology of the present invention for enhancement of central vision (for the macular degeneration case) and other blindness conditions, the initial mapping of the UFOV (Usable Field of Vision) must be digitally generated. It should be noted that the present invention is not limited to mapping from a center area to a peripheral area. In some cases, peripheral vision is affected and the mapping may be from the peripheral area to the center. There are a multitude of methods to accomplish this task. In all cases the initial examination, mapping and calibration must be converted to a digital file. This digital file is then used to construct the boundaries of the UFOV. The UFOV is treated as a sharp outline where peripheral or useable vision is clear, and not degraded. However, this boundary may be a result of evaluation and determination of the gradation of the partial vision, then interpreted to construct the UFOV boundary. This UFOV boundary is then utilized as the baseline for the IMA (Image Mapping Algorithm) to determine the area where the effective central vision can be mapped into, along with the existing effective peripheral vision. There are numerous ways to construct the initial UFOV boundary conditions, both through direct digital means and by manual approaches that can be then converted to a digital file. In some of these cases, the FOV test may be administered by a trained medical professional such as an optometrist or ophthalmologist in the doctor's office. In other cases, an automated FOV test may be self-administered with the proper digital technology. In the third case, a trained professional can manually administer an FOV mapping test to generate the UFOV. Any, and all, of these cases can be utilized to generate the UFOV as outlined.

Figure 22:
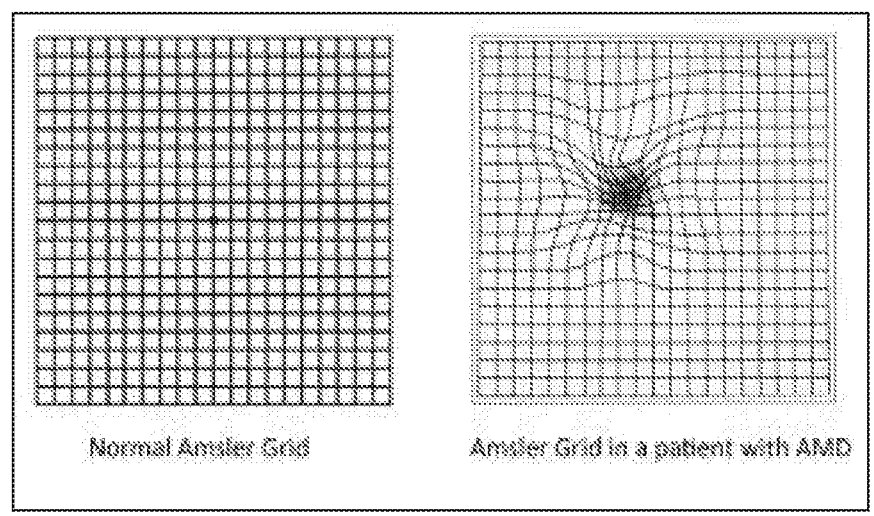
FIG. 22 is a graphic illustration of an Amsler map of a patient with normal vision and an Amsler map of a patient with (Age-related Macular Degeneration) AMD.

In another embodiment, the output of a wearable FOV test is used. For example, the embodiment may use an automated program embedded in the wearable HMD/HUD display device 50, 60. An initial start-up and mapping routine would be performed by observation, such as looking at an Amsler grid or moving objects to check the UFOV, or both, utilizing an existing FOV map to modify and optimize. Eye tracking technology may be used to ensure more accurate FOV mapping and validating fixation. This result is immediately usable directly as the digital input for the UFOV for the Matrix Mapping Technology. A sample Amsler grid of a person with normal vision and a sample Amsler grid of a person with AMD are shown in FIG. 22.

Figure 18:
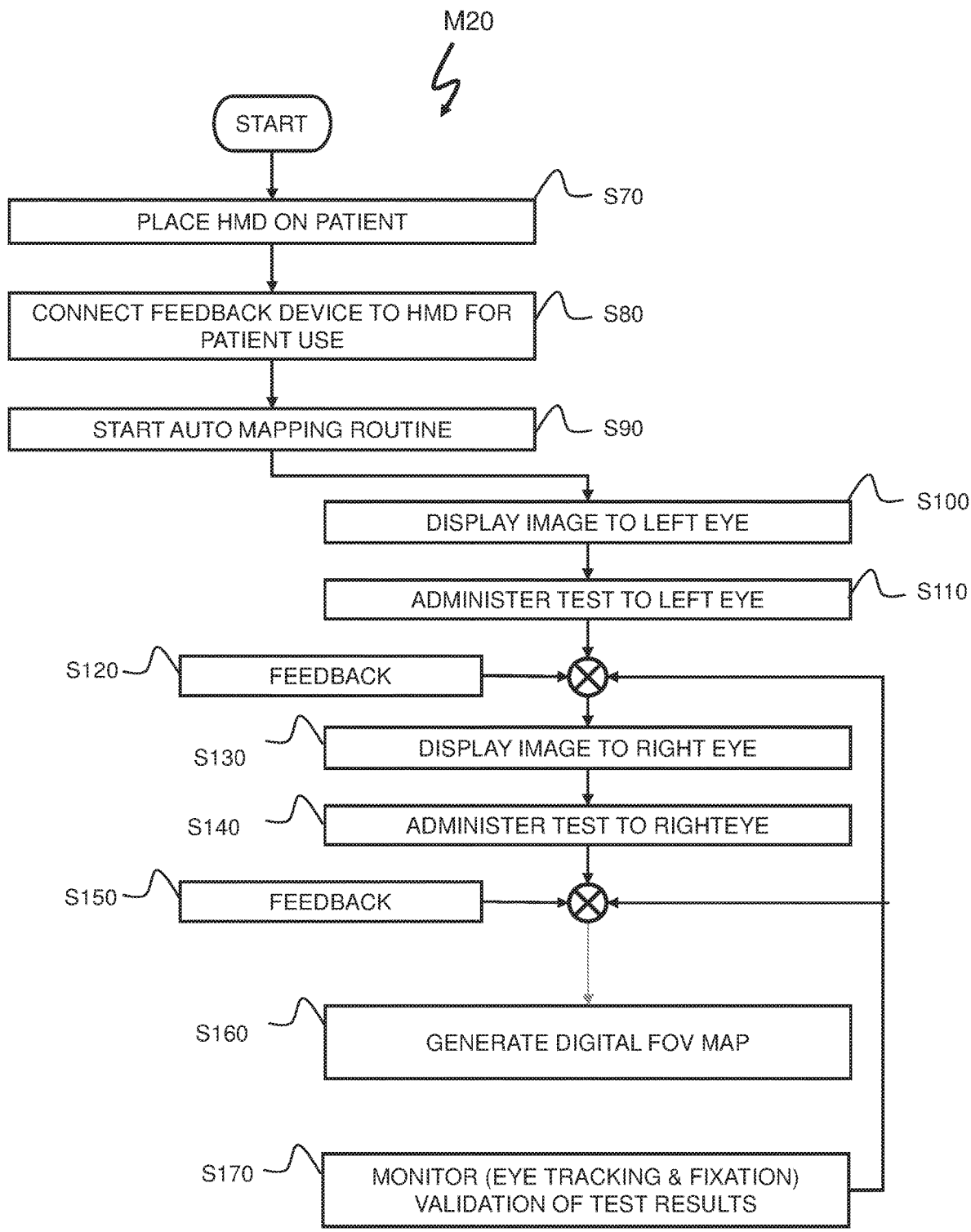
FIG. 18 is a flow diagram of a process for establishing a digital field of vision map, according to an embodiment of the present invention.

With respect to FIG. 18, the general process is embodied in a method M20. The general process is as follows:

1. The wearable HMD (Head Mounted Display) is placed on the patient's head and would be put into "calibration" mode for FOV mapping. (Step S70)

2. The wearable HMD is connected (via external cable or wireless communication mode) to a patient feedback device, such as a PC with a mouse, tablet, mobile phone. (Step S80) or voice recognition technology where the patient gives verbal feedback to the system, which recognized commands, clues and instructions, and accomplishes the FOV mapping automatically.

3. The auto mapping routine is initialized. (Step S90)

4. Eye tracking and fixation are monitored throughout the FOV mapping process in order to determine valid results. Given that Macular Degeneration attacks the central vision, it is important that the fixation and focal point test is administered through markers or objects in the peripheral vision, as well. The valid results can be driven with a secondary feedback loop by constantly monitoring fixation and using only valid visual data points for the mapping of the UFOV and retesting as necessary to develop the entire UFOV map. (Step S170)

Figure 19:
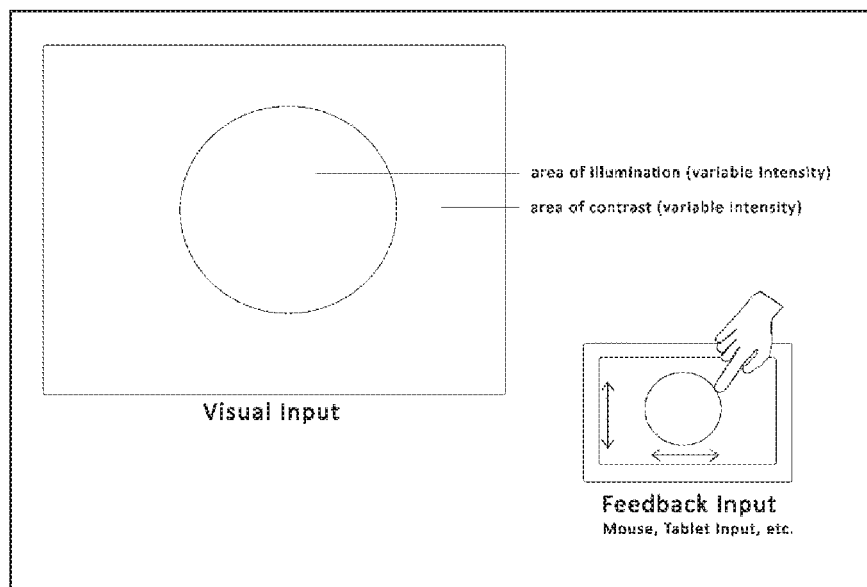
FIG. 19 is a graphical illustration of a first portion of the process of FIG. 18.
Figure 20:
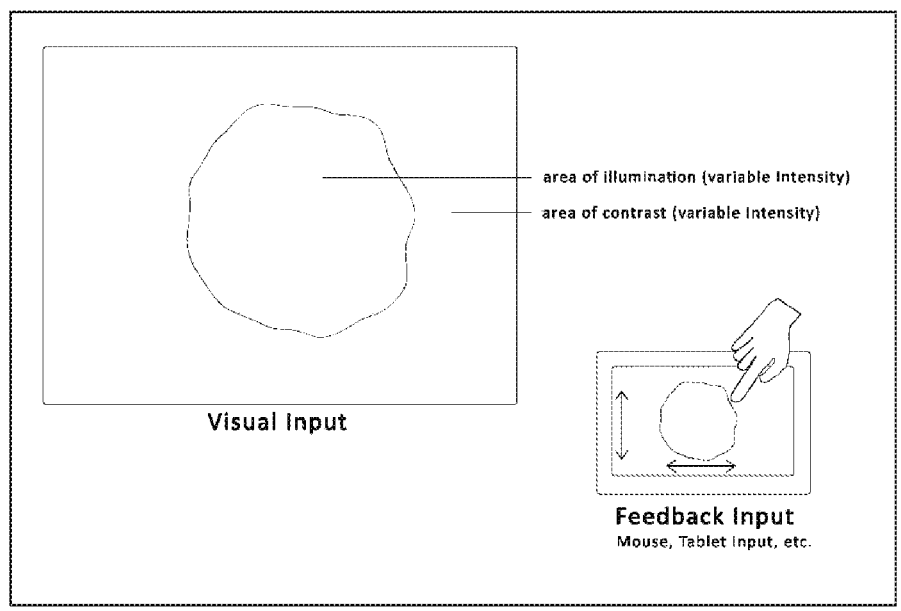
FIG. 20 is a graphical illustration of a second portion of the process of FIG. 18.
Figure 21:
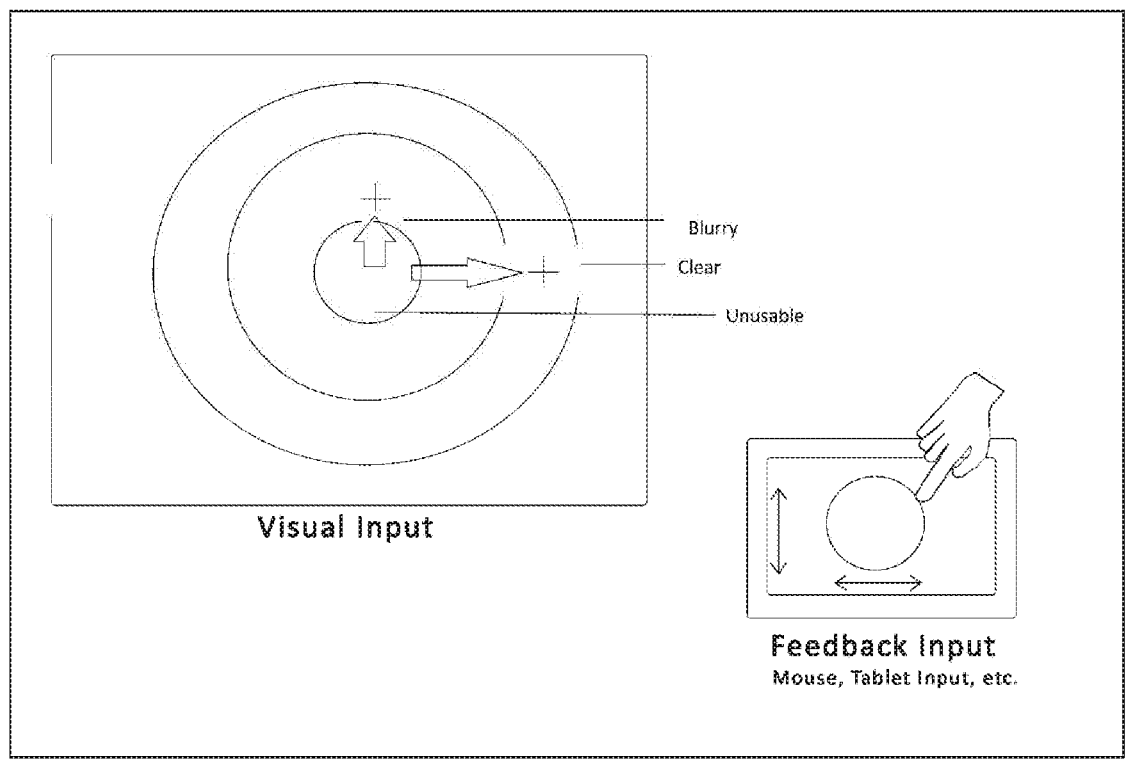
FIG. 21 is a graphical illustration of a third portion of the process of FIG. 18.

5. The FOV mapping test is administered first for the left eye (or right eye) through use of visually moving along an Amsler grid to see where images are warped or straight. (Steps S100 and S110). Alternatively, a flashing object is generated to show at different points in the patient's vision in order to determine visual acuity through the feedback device. This is performed at different level intensities to verify level of degradation of vision. See FIGS. 19 and 20. Alternatively, an object is moved through a series of sequences and with feedback, determined when the object becomes clear from blurry to unviewable, effectively creating gradations of the sight map. See FIG. 21. Alternatively, a constantly expanding sphere is displayed until the edges become clearly visible to the patient. The edges are manipulated through the feedback device until the edge of the UFOV is determined. The latter two cases offer the advantage of a faster approach to FOV mapping for utilization with the wearable later. With a quicker mapping procedure, the system is less likely to cause fixation errors due to lack of concentration from the patient. This also offers quicker calibration for more frequent tweaks to the UFOV map to optimize the performance. The further advantage that can be realized with the patient's ability to manipulate the FOV edge is to better personalize the calibration to their particular affliction (Step S120).

6. The same test is then administered for the other eye (Steps S130, S140, S150).

7. The results are validated or invalidated based on verifying eye tracking and fixation, which is done concurrently while administering the eye tests (Step 170).

8. The Digital FOV map is then generated (Step 160). The auto-mapping and Digital FOV map can be created using voice recognition technology where the patient gives verbal feedback to the system, which recognized commands, clues and instructions, and accomplishes the FOV mapping automatically.

INDUSTRIAL APPLICABILITY

With reference to the drawings and in operation, the present invention provides systems, and methods to stretch, skew and manipulate the image being projected on the eye to avoid the macula, and be directed to the retina's peripheral receptors. Alternatively, the image can be skewed to other portions of the retina. In this way, the entire image is projected on the functioning retinal receptors, and any involvement of the macula is avoided. The systems and methods, according to embodiments of the present invention, create a distortion map of the entire image and project it onto the periphery of the eye, while avoiding the macula. This can be done by the use of computer aided 90-degree 3D or similar High Definition goggles or glasses, or by photon projection with a virtual retina display of the image directly onto the retina of the eye.

The present invention improves the current technique of implantation into the actual eye. Implantation into the eye requires a surgical procedure involving removing the eye's natural lens, as with cataract surgery, and replacing the lens with a tiny telescope, called an Implantable Miniature Telescope (IMT), which works like the telephoto lens of a camera. The IMT is implanted behind the iris, the colored, muscular ring around the pupil. This process, which is expensive, costing up to $15,000 for an operation, doesn't cure AMD, it only helps improve the vision of patients to a certain extent. However, there are numerous drawbacks including infection, surgery complications and loss of the person's lenses. Another of the drawbacks of the IMT is that telescopes are hard to adjust once it has been implanted and must depend on an external battery and device which must be worn by the patient. Suffice it to say, this technology is invasive, requires that the patient's own lenses be removed, is not reversible and requires both surgery and extensive rehabilitation. Furthermore, the rehabilitation process is extensive and involves training patients to effectively use the device. Rehabilitation post-surgery takes about six months to a year.

In some embodiments of the invention, the method and manner of the skewed projection relies on external lenses, like Google Glass, Oculus Rift, Magic Leap, or Meta. These High Definition goggles or glasses like Google Glass, Oculus Rift, Magic Leap or Meta, have developed commercially deployed displays with up to 2 million pixels, a resolution seen only otherwise on ultra-high-definition TVs and tablet computers, which provide the resolution needed to put the entire image on the peripheral retina receptors in sufficient detail to be analyzed by the optical nerve and brain.

Also, for the introduction of perspective, two cameras can to be used, and the modern goggles and glasses can accept more than one image interface and/or signal. Thus, the computed manipulated images are captured in real-time and displayed in real-time for the patient.

In addition, the goggles and/or glasses could be used to house a technology like virtual retina display, retina scan display projection, and/or a retinal projector technology which all use photon on retina projection, which in this case would be modulated by the IDM (Image Distortion Map) to the person's specific Retinal Map so that an intentionally distorted image would be projected onto the areas of the eye which have the best visual reception. In this fashion, you can project the image directly into the portion of the peripheral retina which is still active in an MD patient via photons, utilizing a technology such as a virtual retinal display (VRD), also known as a retinal scan display (RSD) or retinal projector (RP), is used. When combined with these technologies, the person's specific retinal map, modulated by the image distortion map, would be displayed by the technology which draws a raster display (like a television) directly onto the retina of the eye, and in this case on to the usable portions of the retina of the eye. With the VRD, RSD or RP, the patient user sees what appears to be a conventional display floating in space in front of them, which is corrected for the loss of macula, but still provides the patient with the ability to see other peripheral obstacles, such as steps in front of the patient which the camera is not yet focused on.

Another advantage is that these types of wide field-of-vision goggles or glasses can be used in conjunction with one or more cameras, which are typically head mounted. Another advantage of these types of glasses is that they can be combined with proximity sensors, motion sensors, head and eye tracking, a feature which is advantageous for understanding a user's specific field of vision for adjustments, and to measure distance through triangulation. For instance, in human eyes there is a convergence of the image when it comes closer to the face, meaning that the image captured by each eye begins to overlap the other eye's image. In 3D camera applications, this convergence is not always taken into account, and the sensors can also be used to automatically change the field of view presented to the retina, i.e., a virtual zoom to determine facial features when in proximate distance of another person. When used in conjunction with a user interface, the zoom, skew or other manipulation features can be selected in a straightforward method chosen by the user to gain visual acuity in various environments. A differential adjustment may also be chosen with regard to each eye. Alternatively, software derived proximity and motion sensing can be employed by utilizing comparative techniques on sequential camera images.

Thus, this invention teaches that one camera can be used for monoscopic image capture and display. In addition, this invention teaches that you can use two cameras to simulate on the goggles/glasses display true stereoscopic vision, wherein the IDM (Image Distortion Map) model includes factor correction for epipolar curves, guided by the epipolar geometry so that stereo vision, generated by two or more cameras, can be employed and be displayed, and seen.

The invention uses computer aided video images which are skewed and stretched in a matrix distortion or other similar fashion to put the most or the entirety of the image onto the peripheral vision of the patient by opening up the center of the image and manipulating it to the peripheral cones of the eyes, as seen by the patient in the projected image, in order to project the video captured images on the peripheries of the cones in the eyes where vision is still active. The benefits of this invention are that no invasive procedures are necessary and as the MD changes, the software can be adjusted so that the image is now correctly skewed. It is an additional advantage of this invention that live feedback can be provided.

In the fashion taught by this invention, the viewed experience makes it nearly impossible for the user to distinguish between what is actually seen and the image that is created by the distortion map.

Thus, the spreading and/or multi-lateral skewing of the image which reflects the corrected image onto 3D or High-Definition goggles and/or glasses worn by the patient. The image is skewed via the IDM (Image Distortion Map) module to avoid projection to the area of the eye which involves the macula, but still has all the image information. To imagine this process, think of a picture which is printed onto a stretchable and compactable substance. A hole is cut into the middle of the image and stretched open. This makes the image compress into the sides of the picture. Thus, all of the information of the picture is still there, it is just rearranged where a hole is in the middle and the image is moved each way to the side, top and bottom. This "hole-cutting" is done via algorithms and computer software/firmware technology, for instance, using a technology like Image Distortion Mapping as above mentioned.

Matrix Distortion of a camera and Matrix Calibration, are the correction of the distortion and are commonly known areas of camera calibration. Oftentimes, cameras display a significant distortion. However, the distortion is constant, like on a matrix, and with a calibration and some remapping, the distortion can be corrected. Typical distortion correction takes into account the radial and tangential factors. For the radial factor, one uses the following formulas:

$$x_{corrected}=x(1+k_1r^2+k_2r^4+k_2r^6)$$

$$y_{corrected}=y(1+k_1r^2+k_2r^4+k_2r^6),$$

where r is defined by r=x2 and y2 and $k_1$ and $k_2$ are defined by the coefficients in the retinal map. The corrected x and y values are designed to create a corrected position for the pixels in an image, where x and y defined the original position of the uncorrected image pixel and $x_{corrected}$ and $y_{corrected}$ are the corrected position of the pixel. The purpose of the mapping is to take a three-dimensional model of active vision, defined by one of the mapping processes described above, and applying the model to a two-dimensional image, such that a pixel on the two-dimensional image is mapped to the corrected location of the pixel after applying the function containing the specific three-dimensional mapping.

In one embodiment, the process maps each pixel in the two-dimensional image (or video) from the camera(s) and maps the pixel to a new pixel location on the display. In another embodiment, only the data points are remapped. The other image data is transformed using a predefined function that interpolates the data between the data points.

So, for an old pixel point at (x,y) coordinates in the input image, its position on the corrected output image will be (x_{corrected} y_{corrected}). This corrects for the presence of the radial distortion which manifests in the form of the "barrel" or "fish-eye" effect. Tangential distortion occurs because the image taking lenses are not perfectly parallel to the imaging plane. It can be corrected via the formulas:

$$x_{corrected}=x+[2p_1xy+p2(r^2+2x^2)], \text{ and}$$

$$y_{corrected}=y+[p_2xy+p(r^2+2y^2)].$$

However, for this invention a type of reverse methodology is employed that would not normally be thought of Thus, once typical distortions in the camera have been fixed, then it is the teaching of this invention that an intentional distortion is introduced. In one embodiment, the IDM (Image Distortion Map) model stretches a center pixel to the points at which an individual cannot see and compresses everything else to fit in the remaining peripheral portion of the goggles. In this fashion, a "hole" is artificially cut into the image by computer and software/firmware aided manipulation such that a pixel, which was formerly in the center of an image, is squeezed to the outside so that the entire image is projected around the "hole" in the center which is artificially created. Only the matrix distortion portion of the model is shown here, as the other pieces are not directly related to the IDM model, but are other substantive parts of this program for projecting the image once the IDM model is applied. As shown, the IDM distortion model is shown as a value to the "webGL"1, a program which can be used with "renderingContext"2. These are only some of the protocols which could be used, thus the actual IDM model will change with whatever device is used to do the actual processing.

"WebGL" is a JavaScript API for rendering interactive 3D computer graphics and 2D graphics within any compatible web browser without the use of plug-ins. WebGL is based on OpenGL ES 2.0 and provides an API for 3D graphics. "RenderingContext" is a helper type representing any of the following rendering contexts: CanvasRenderingContext2D, WebGLRenderingContext or WebGL2RenderingContext (which inherits from WebGLRenderingContext).

Samples of the IDM model distortion in webGL can be created as follows:

vec2*hWa*(vec2in01){vec2*tHt*=(in01−1*Cr*)*sin;

float *rSq*=(*tHt.x*tHt.x*)+(*tHt.y*tHt.y*);

vec2*pRi*=*tHt**(*hWp.x*+*hWp.y***rSq*+*hWp.z*rSq*rSq*+ *hWp.w*rSq*rSq***rSq*);

return 1*Cr*+*sLe***pRi*;}

The hWa method as listed above will take a few input variables describing the image center as it pertains to the particular display device, and it returns a specific Uniform Location value to enable the IDM device to render the corrected projection to the display device. It does all the math to provide the distortion matrix to, in this case, the openGL graphics driver. The method takes input values regarding the field of view of the goggles, which are different in different models, and the pupillary distance, and returns the distortion matrix, as a floating point, back to the image processor. As shown above, the variables used are specifically to apply to a webGL context, which is only one of many possible implementations. The hWa method takes an input variable that describes the image center as it pertains to the particular display device (like an Oculus Rift), and it returns a specific Uniform Location value to enable the IDM device to render the corrected projection to the display device.

The IDM model takes vector values (numbers) that describe the lens center of the goggle device (per eye, on the oculus rift) (called "1Cr"), as well as field of view of the display, and returns the vector object that defines how to distort the image to make it more viewable by someone with macular degeneration. The key element is to define the mapping between image (pixel) coordinates and 3D rays in the camera(s) coordinates as a linear combination of non-linear functions of the image coordinates. This allows a linear algorithm to estimate nonlinear models, and creates a method to distort the image such that there is typically a (circular) "hole(s)" or a "cut-out(S)", or a geometrically distorted area in the center of the image accomplished by moving the pixel coordinates so that the entire image is distorted and mapped around the hole which is cut-out or to compensate for the geometric distortion caused by leaking vessels. How this image is exactly cut-out and the pixels rearranged is accomplished through testing with the subject so that it is attempted to use as many peripheral retina receptors as that subject has active. This Image Distortion Map ("IDM") model thus becomes that person's Prescribed Retinal Interface ("PRI").

This invention has great benefits in that it is non-invasive, can be worn or not worn, and is easier to adjust and keep fine-tuned because it is external, and image and algorithms which stretch and skew the image to the PRI can be adjusted in real-time based on MD Patient feedback in adjustments.

In another embodiment of the invention, the active retinal receptors are identified through evaluation with the system or by known prescription whereby the lowest number of receptors in the retina required to effect the desired mental and visual impression of the image are used to increase the apparent refresh rate, by actually increasing the refresh rate by displaying the image on less than all of the receptors.

In another aspect of the present invention, various FOV maps are stored and/or analyzed or tracked in a database. The database could be stored in the cloud. A knowledge base based be used to analyze the FOV maps, and one or more of the FOV maps could be used as a starting point for a patient. The selected FOV map could be fine-tuned using one or more of the methods described above. A FOV from the database may be chosen as a starting point based on patient visual models, common trends and outliers within the data. The FOVs models could be sorted and/or chosen based on identified common boundaries. The output of the different FOV maps, i.e., the resultant corrected images could be analyzed, with patient input, utilizing a process of comparison and elimination while viewing desired real world images, i.e., a face chart, text chart or the like.

In another aspect of the present invention, the system may provide for in-home monitoring of the patient's vision. The patient's FOV may be mapped periodically, such as daily or as often as desired. The patient's FOV may be mapped according to method M20 described above, utilizing the wearable HUD, or otherwise as desired. Test results may be sent to the database, which may be cloud-based, where they may be analyzed and compared. If certain criteria are met, for example if the volumetric size of the patient's scotoma per eye increases or there now show areas of no sight in areas where there originally was sight, then a message or alert may be sent to the patient's ophthalmologist or retinal surgeon. For example, the message or alert may be sent to the ophthalmologist or retinal surgeon's patent case software, indicating that the physician needs to look at the changes to see if there might be a new bleed. If a new bleed is dealt with immediately, the patient's additional retina may be saved, whereas on the other hand if the bleed were discovered at the patent's next appointment in 6 months, the damage may be permanent.

A controller, computing device, server or computer, such as described herein, includes at least one or more processors or processing units and a system memory, which may be an embodiment in a personal computer, server, or other computing device. The controller typically also includes at least some form of computer-readable media. By way of example and not limitation, computer-readable media may include computer storage media and communication media. Computer storage media may include volatile and nonvolatile, removable and non-removable media implemented in any method or technology that enables storage of information, such as computer readable instructions, data structures, program modules, or other data. Communication media typically embody computer-readable instructions, data structures, program modules, or other data in a modulated data signal, such as a carrier wave or other transport mechanism and include any information delivery media. Those skilled in the art should be familiar with the modulated data signal, which has one or more of its characteristics set or changed in such a manner as to encode information in the signal. Combinations of any of the above are also included within the scope of computer-readable media.

The order of execution or performance of the operations in the embodiments of the invention illustrated and described herein is not essential, unless otherwise specified. That is, the operations described herein may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

In some embodiments, a processor or controller, as described herein, includes any programmable system including systems and microcontrollers, reduced instruction set circuits (RISC), application specific integrated circuits (ASIC), programmable logic circuits (PLC), and any other circuit or processor capable of executing the functions described herein. The above examples are exemplary only, and thus are not intended to limit in any way the definition and/or meaning of the term "processor."

The above description of illustrated examples of the present invention, including what is described in the Abstract, are not intended to be exhaustive or to be limited to the precise forms disclosed. While specific embodiments of, and examples for, the invention are described herein for illustrative purposes, various equivalent modifications are possible without departing from the broader spirit and scope of the present invention.

What is claimed is:

1. A method of at-home monitoring of eye conditions, the method comprising:
    providing a system to a patient, the system comprising a database and a model controller where:
    the model controller is configured to establish a visual model associated with the patient and to store the visual model in the database;
    the visual model includes data related to a quality of the patient's vision;
    the data includes data acquired using eye tracking;
    the model controller is further configured to establish a boundary as a function of the data associated with the visual model, the boundary being indicative of an area to be corrected within the patient's vision; and
    the model controller is further configured to establish a retinal map as a function of the boundary and store the retinal map in the database;
    testing the patient's eyes with the system to produce the visual model;
    comparing the visual model with prior visual models to detect changes; and
    notifying a physician of the changes;
    where the database is cloud-based;
    where the visual model is established using a computer-based system contained in a head mounted display.

2. The method of claim 1 where the visual model is established using a computer-based system contained in an Augmented Reality head mounted display.

3. The method of claim 1 where the visual model is established using a computer-based system contained in a mobile phone.

4. The method of claim 1 where testing the patient's eyes occurs regularly.

5. The method of claim 1 where notifying the physician of the changes occurs when the changes meet designated criteria.

6. The method of claim 1 where notifying the physician of the changes occurs via radio frequency transmission.

7. The method of claim 1 where testing the patent's eyes is performed by the patient.

8. The method of claim 1 where testing the patient's eyes is performed at the patient's home.

9. The method of claim 1 where the physician is notified remotely if certain criteria indicating deterioration in the eye occurs.

\* \* \* \* \*